United States Patent
Kim et al.

(10) Patent No.: US 7,935,678 B2
(45) Date of Patent: May 3, 2011

(54) THERAPEUTIC USE OF CPG OLIGODEOXYNUCLEOTIDE FOR SKIN DISEASE

(75) Inventors: Tae-Yoon Kim, Seoul (KR); Doo-Sik Kim, Seoul (KR); Hyung-Joo Kwon, Chungcheongbuk-do (KR); Yang-Soon Kim, Seoul (KR)

(73) Assignees: Bio Clue & Solutions Co, Ltd., Seoul (KR); Dong-Heon Shin, Seoul (KR); Tae-Yoon Kim, Seoul (KR)

( * ) Notice: Subject to any disclaimer, the term of this patent is extended or adjusted under 35 U.S.C. 154(b) by 44 days.

(21) Appl. No.: 10/589,102

(22) PCT Filed: Nov. 4, 2005

(86) PCT No.: PCT/KR2005/003717
§ 371 (c)(1),
(2), (4) Date: Oct. 5, 2007

(87) PCT Pub. No.: WO2006/049454
PCT Pub. Date: May 11, 2006

(65) Prior Publication Data
US 2009/0062224 A1    Mar. 5, 2009

(30) Foreign Application Priority Data
Nov. 5, 2004 (KR) .................. 10-2004-0090000

(51) Int. Cl.
*A61K 48/00* (2006.01)
*C07H 21/02* (2006.01)
(52) U.S. Cl. ................... 514/44 R; 536/23.1
(58) Field of Classification Search ............... 514/44 R; 536/23.1
See application file for complete search history.

(56) References Cited

U.S. PATENT DOCUMENTS

| | | | |
|---|---|---|---|
| 4,458,066 A | 7/1984 | Carauthers et al. | |
| 4,469,863 A | 9/1984 | Ts'o et al. | |
| 4,650,675 A | 3/1987 | Borel et al. | |
| 5,023,243 A | 6/1991 | Tullis | |
| 2003/0233675 A1* | 12/2003 | Cao et al. | 800/279 |
| 2007/0015271 A1* | 1/2007 | Rosen et al. | 435/252.1 |

FOREIGN PATENT DOCUMENTS

| | | |
|---|---|---|
| EP | 0092574 | 4/1992 |
| WO | 1998/029124 | 7/1998 |
| WO | 2001/093905 | 12/2001 |
| WO | 2004/078772 | 9/2004 |

OTHER PUBLICATIONS

Najar and Dutz. J Invest Derm 128:2204-2210, 2008.*
Hussain and Kline. J Invest Dermatol Symp Proc 9:23-28, 2004.*
Tokura. J Dermatol Sci 58:1-7, 2010.*
Balles et al. J Immunol 167:4878-4886, 2001.*
Immune Response definition printout from http://dictionary.reference.com/browse/immune+response, printed out Jul. 28, 2010, p. 1.*
Gilkeson, GS. et al., Induction of Cross-Reactive Anti-dsDNA Antibodies in Preautoimmune NZB/NZW Mice by Immunization with Bacterial DNA, J. Clin. Invest., 1995, 95:1398-1402.
Krieg, AM. et al., CpG motifs in bacterial DNA trigger direct B-cell activation, Nature 374:546-549, 1995.
Akdis, CA. "Immune regulation in atopic dermatitis ," Curr Opin Immunol., 2000 12:641-646.
Krieg, AM. "CpG Motifs in Bacterial DNA and Their Immune Effects," Annual Review Immunol., 2002, 20: 709-760.
Warren, TL et al.,"APC Stimulated by CpG Oligodeoxynucleotide Enhance Activation of MHC Class I-Restricted T Cells1," J. Immunol., 2000, 165:6244-6251.
Kwon, HJ. et al., "NF-KB-dependellt regulation of tumor necrosis factor-C'L gene expression by CpG oligodeoxynucleotides," Biochem. Biophys. Res. Commun, 2003, 311:129-138.
Lee, KW. et al.,"CG sequence- and phosphorothioate backbone modification-dependent activation of the NF-KB-responsive gene expression by CpG-oligodeoxynucleotides in human RPMI 8226 B cells," Mol. Immunol, 2004, 41:955-964.
Deng GM et al., "The features of arthritis induced by CpG motifs in bacterial DNA," Arthritis & Rheumatisum, 2000, 43 (2):356-364.
Masayuki Miayta et al., "Unmethylated Oligo-DNA Containing CpG Motifs Aggravates Collagen-Induced Arthritis in Mice," Arthritis & Rheumatisum, 43(11):2578-2582, 2000.
Tanaka, T. et al., "An Antisense Oligonucleotide Complementary to a Sequence in I'y2b Increases 3'2b Germllne Transcripts, Stimulates B Cell DNA Synthesis, and Inhibits Immunoglobulin Secretion," J Exp. Med. 1992, 75:597-607.
Hans-Joachim Anders et al., "Activation of toll-like receptor-9 induces, progression of renal disease in MRL-Fas(Ipr) mice," The FASEB Journal express article 10. 1096/fj. 03-0646fje. published online Jan. 20, 2004.
Tsunoda I. et al., "Exacerbation of viral and autoimmune animal models for multiple sclerosis by bacterial DNA.," Brain Pathol. 1999, 9(3):481-493.
Bachmaier K. et al., "Chlamydia Infections and Heart Disease Linked Through Antigenic Mimicry," Science, 1999, 283(5406):1335-1339.
D'Andrea A et al., "Production of natural killer cell stimulatory factor (interleukin 12) by peripheral blood mononuclear cells," J. Exp. Med., 1992, 176:1387. Sato T et al., Immunostimulatory DNA Sequences Necessary for Effective Intradermal Gene Immunization, Science 1996, 273:352-354.
Shu U et al., "Activated T cells induce interleukin-12 production by monocytes via CD4O-CD40 ligand interaction," Eur. J. Immunol., 1995, 25:1125-1128.
Cella M et al.,"Ligation of CD40 on dendritic cells triggers production of high levels of interleukin-12 and enhances T cell stimulatory capacity: T-T help via APC activation," J. Exp. Med., 1996, 184:747-752.

(Continued)

*Primary Examiner* — Thaian N Ton
*Assistant Examiner* — Marcia S Noble
(74) *Attorney, Agent, or Firm* — Casimir Jone, S.C.

(57) ABSTRACT

Disclosed is the therapeutic use of CpG oligodeoxynucleotides for skin diseases. The CpG oligodeoxynucleotides (CpG ODNs) of the present invention show excellent immunoactive effects against skin diseases in both cases of CpG ODNs with a phosphorothioate backbone and CpG ODNs with a phosphodiester backbone.

9 Claims, 17 Drawing Sheets

OTHER PUBLICATIONS

Chan SH et al., "Induction of interferon gamma production by natural killer cell stimulatory factor: characterization of the responder cells and synergy with other inducers," J. Exp. Med., 1991, 173:869-879.

Neumann C., et al., "Comparative analysis of the frequency of house dust mite specific and nonspecific Th1 and Th2 cells in skin lesions and peripheral blood of patients with atopic dermatitis," J Mol Med., 74: 401-406, 1996.

Aiba S., et al., "Alteration in the production of IL-10 and IL-12 and aberrant expression of CD23, CD83 and CD86 by monocytes or monocyte-derived dendritic cells from atopic dermatitis patients," Exp Dermatol., 2003, 12: 86-95.

Nilsson C., et al.,"Low numbers of interleukin-12-producing cord blood mononuclear cells and immunoglobulin E sensitization in early childhood.," Clin Exp Allergy., 2004, 34: 373-380.

Katakura, T., et al., "A combination therapy using IL-12 and soluble IL-4 receptor on herpes simplex virus Type 1 infection in a human-SCID chimera model of thermal injury," Clin. Immunol. 2002, 105:363-370.

Hengge U. R., et al., "Topical immunomodulators for the treatment of external genital warts, cutaneous warts and molluscum contagiosum," Br. J. Dermatol., 2003, 149:15-19.

Arany I., et al., "Enhancement of the innate and cellular immune response in patients with genital warts treated with topical imiquimod cream 5%,"Antiviral Res., 1999, 43: 55-63.

Rook AH., et al "The potential therapeutic role of interleukin-12 in cutaneous T-cell lymphoma," Ann. N. Y. Acad. Sci., 1996, 795:310-318.

Gollob, JA., et al.,"Phase I Trial of Concurrent Twice-Weekly Recombinant Human Interleukin-12 Plus Low-Dose IL-2 in Patients With Melanoma or Renal Cell Carcinoma," J. Clin. Oncol., 2003, 21:2564-2573.

Trinchieri G., et al., "Interleukin-12: a proinflammatory cytokine with immunoregulatory functions that bridge innate resistance and antigen-specific adaptive immunity," Annu Rev Immunol., 1995, 13: 251-276.

Krepler C., et al., "CpG oligonucleotides elicit antitumor responses in a human melanoma NOD/SCID xenotransplantation model," J. Invest Dermatol., 2004, 122: 387-391.

Vestergaard, C., et al., Overproduction of Th2-specific chemokines in NC/Nga mice exhibiting atopic dermatitis-like lesions, J Clin Invest 104:1907-1105, 1999.

Matsuo, R., et al., "Interleukin-12 protects thermally injured mice from herpes simplex virus type 1 infection," 1996, 59:623-630.

* cited by examiner

A

B

AD              oligo-4(O)

CD4

CD8

THERAPEUTIC USE OF CPG OLIGODEOXYNUCLEOTIDE FOR SKIN DISEASE

FIELD OF THE INVENTION

This application claims priority to a Korean Patent Application No. 10-2004-0090000, filed on Nov. 5, 2004, the contents of which are hereby incorporated by reference.

The present invention relates to therapeutic use of CpG oligodeoxynucleotides for skin diseases.

BACKGROUND OF THE INVENTION

Skin disease refers to all disorders occurring on the skin of animals including humans. Among skin diseases, atopic dermatitis is a chronic/inflammatory skin disease, whose main symptoms include serious itching, skin dryness and eczema (Rudikoff, D. et al., *Lancet.* 351:1715-1721, 1998). Generally, atopic dermatitis is hereditary, and is accompanied with allergic asthma, allergic rhinitis, allergic conjunctivitis and urticaria depending on individual characteristics. Reported symptoms related to immunological disorders occurring in patients suffering from atopic dermatitis includes: increased production of IgE, reduced number of Th1 (T-cell Helper type 1) lymphocytes secreting IFN-γ, or the like. Additionally, when viewed from the histological point of view, skin lesions of atopic dermatitis show the increase of T lymphocytes having a $CD4^+$ phenotype, infiltration of monocyte cells/macrophages, and mast cells and eosinophils. Also, skin lesions of atopic dermatitis show the increase of dendritic cells (DCs) and epidermal Langerhans cells (Imokawa, G., et al., *J. Invest. Dermatol.*, 96:523-526, 1991). It has been reported that such conditions occur in normal skin sites as well as lesions (Leung D Y, Bhan A K, Schneeberger E E, Geha R S. *J Allergy Clin Immunol.*, 71 (1 Pt 1), 47-56, 1983). Recently, it was reported that the number of CCR-4 expressing memory $CD4^+$ T lymphocytes increase in lesions of atopic dermatitis (Imai, T. et al., *Int. Immunol.*, 11:81-88, 1999). Additionally, it was reported by Van der Heijden F L et al. that T lymphocytes having a $CD4^+$ phenotype, infiltrated into the lesions, release IL-4 (Van der Heijden F L et al., *J Invest Dermatol.*, 97:389-394, 1991), and the IL-4 serves to accelerate low-affinity Fc receptors to immunoglobuline E in antigen presenting cells.

Further, experimental results showing that T lymphocytes as well as various cytokines released therefrom are closely related to the immunolopathogenic mechanism of atopic dermatitis, were reported recently. Also, it was reported that allergen-specific T helper type 2 lymphocytes producing IL-4, IL-5 and IL-10 increase in the lesions of patients suffering from atopic dermatitis, resulting in a significant effect upon both allergic reactions and an increase of IgE (hussain, I. et al., *Curr Drug Targets Inflamm Allergy.*, 2: 199-120, 2003). Meanwhile, other researchers have studied the effect of atopic dermatitis-related chemokines and receptors thereof upon skin barriers. As a result, it was reported that a great amount of TSLP (thymic stromal lymphopoietin) and MDC (macrophage-derived chemokine) are produced from keratinocytes of patients suffering from atopic dermatitis, and a great amount of RANTES, TARC and MDC are produced upon stimulation of IFN-γ (Giustizieri, M L., et al., *J. Allergy Clin Immunol.*, 107:871-877, 2001).

In general, the immune system of the vertebrate have developed evolutionary in such a manner that immunoactivity arises rapidly in response to the attack of microorganisms through the recognition of several kinds of characteristic molecules in microorganisms. According to studies of many researchers, it was shown that bacterial DNA has various structural determining factors, which are not present in the DNA of the vertebrate, and such factors activates immune cells (Gillkeson, G S. et al., *J. Clin. Invest.*, 95:1398-1402, 1995). The significant difference between the vertebrate DNA and the bacterial DNA is that genomes of the vertebrata have suppressed CpG dinucleotide and 70% of cytosine is methylated in the CpG motif (Krieg, A M. et al., *Nature* 374:546-549, 1995). Unlike mammals, unmethylated CpG motifs are abundant in bacteria. Oligodeoxynutleotides (ODNs) comprising CpG motifs activate the protection mechanism of a host, which ranges from the innate immune response to the acquired immune response (Akdis, C A. *Curr Opin Immunol.*, 12:641-646, 2000). In general, CpG ODNs can activate B cells as well as NK cells. Additionally, the CpG sequence stimulates macrophage in order to secrete IL-12, which is a latent derivative for the production of IFN-γ from NK cells (Krieg, A M. Annual Review Immunol., 20: 709-760, 2002). In addition to the above, such cells secrete pro-inflammatory cytokines such as IL-1, IL-6, IL-18 and TNF-α, and cytokines such as IFN-γ and IL-12 which make a Th1-biased immunological environment or chemokines. Moreover, the CpG ODNs enhance humoral responses inducing IgG2a isotypes (Th1 type indicator), and increases activation of cytoxic T lymphocytes (CTL) (Warren, T L. et al., *J. Immunol.*, 165:6244-6251, 2000). Use of the CpG ODNs for the treatment of allergic conditions and cancer in animal models is effective for the enhancement of direct or indirect immune responses. It is known that such CpG ODNs have different physiological activities depending on their nucleotide sequences, even if they have the same CpG motif.

Recently, CpG ODNs having a modified backbone have been developed in order to increase the availability of CpG ODNs. The CpG ODNs with a phosphodiester backbone, i.e. a basic backbone of DNA, are sensitive to nuclease, and thus is degraded in vivo. Therefore, there is little possibility for inducing in vivo toxicity. However, the above CpG ODNs have low activity compared to the CpG ODNs with other backbones (Kwon, H J. et al., *Biochem. Biophys. Res. Commun,* 311:129-138, 2003; and Lee, K W. et al., *Mol. Immunol,* 41:955-964, 2004). On the contrary, CpG ODNs with a phosphorothioate backbone is prepared by artificially modifying its structure so as to prevent its degradation by the nuclease in vivo. The CpG ODNs with a phosphorothioate backbone are more stable in vivo and shows more excellent effect of inducing B cells, compared to the CpG ODNs with a phosphodiester backbone. Therefore, the CpG ODNs that are modified to have a phosphorothioate backbone are widely used. However, the CPG ODNs with a phosphorothioate backbone increase non-specific ODN binding to various proteins, and are not degraded readily in vivo, thereby causing toxicity. Additionally, it is reported that the CpG ODNs with a phosphorothioate backbone cause arthritis and aggravate arthritis conditions (Deng G M et al., *Arthritis & Rheumatisum,* 43(2): 356-364, 2000; Masayuki Miayta et al., *Arthritis & Rheumatisum,* 43(11):2578-2582, 2000), and also can cause autoimmune diseases such as SLE (systemic lupus erythematosis) (Tanaka, T. et al., *J Exp. Med.* 175:597-607, 1992; and Hans-Joachim Anders et al., *The FASEB Journal* express article 10. 1096/fj. 03-0646fje. published online Jan. 20, 2004). In addition to the above reports, many researchers reported side effects of the CpG ODNs with a phosphorothioate backbone (Tsunoda I. et al., *Brain Pathol.,* 9(3):481-493, 1999; and Bachmaier K. et al., *Science,* 283(5406):1335-1339, 1999).

As described above, although there has been widely studied on a use of the CpG ODNs as immunoactivators, any disclosure of the CpG ODNs for use in the prevention and treatment of skin diseases cannot be found. Particularly, the use of the CpG ODNs with a phosphodiester backbone for the prevention and treatment of skin diseases has never been studied.

DISCLOSURE OF THE INVENTION

Therefore, the present invention has been made in view of the above-mentioned problems. It is an object of the present invention to provide novel therapeutic use of a CpG oligodeoxynucleotide.

According to an aspect of the present invention, there is provided a method for inhibiting a Th2 cytokine and/or inducing a Th1-cytokine, which comprises administering to a subject in need thereof an effective amount of a CpG oligodeoxynucleotide represented by the following formula:

[formula]SYYSSACGTTSNYRAWMYTC(SEQ ED NO. 1)

wherein S is G or C; Y is C or T; N is any one selected from the group consisting of A, G, T and C; R is G or A; W is A or T; and M is A or C, and wherein the CpG oligodeoxynucleotide comprises at least two unmethylated CpG motifs.

According to another aspect of the present invention, there is provided a method for stimulating an immune response, which comprises administering to a subject in need thereof an effective amount of the CpG oligodeoxynucleotide.

According to still another aspect of the present invention, there is provided a method for treating or preventing a skin disease, which comprises administering to a subject in need thereof an effective amount of the CpG oligodeoxynucleotide.

DEFINITIONS

Unless defined otherwise, all technical and scientific terms used herein have the same meaning as commonly understood by those of ordinary skill in the art to which this invention pertains. The following references provide one of skill with general definition of many of terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY. In addition, the following definitions are provided to assist the reader in the practice of the invention.

As used herein, the term "CpG motif" means a nucleotide sequence, which contains unmethylated cytosine-guanine dinucleotide linked by a phosphate bond (also referred to as "unmethylated cytosine-phosphate-guanine dinucleotide") and activates the immune response.

As used herein, the term "CpG oligodeoxynucleotide" (referred to as "CpG ODN" hereinafter) means an oligodeoxynucleotide comprising at least two the above CpG motifs.

As used herein, the term "subject" means an animal, particularly a mammal. The subject may be a cell, tissue or organ derived from the animal.

As used herein, the term "effective amount" is referred to as the amount that shows the effects of inhibiting a Th2 cytokine, inducing a Th1 cytokine, activating a dendritic cell, stimulating an immune response, or treating or preventing a skin disease in a subject.

Hereinafter, the present invention will be explained in more detail.

The present inventors have studied the effect of a CpG ODN upon the treatment or prevention of a skin disease, and have found that the CpG oligodeoxynucleotide represented by the following formula is useful as an agent for treating or preventing skin diseases:

[formula]SYYSSACGTTSNYRAWMYTC(SEQ ID NO. 1)

wherein S is G or C; Y is C or T; N is any one selected from the group consisting of A, G, T and C; R is G or A; W is A or T; and M is A or C, and wherein the CpG oligodeoxynucleotide comprises at least two unmethylated CpG motifs.

Preferably, in the above formula, YS or YR dinucleotide may be CG. More preferably, the CpG ODN of the present invention is any one selected from the group consisting of the following SEQ ID NOs. 2-8. Most preferably, the CpG ODN of the present invention may have the nucleotide sequence represented by the following SEQ ID NO. 2 or 8.

The CpG ODN of the present invention may be derived from a natural source (e.g. chromosomal DNA of E. coli). It also may be chemically synthesized or recombinantly constructed. The CpG ODN of the present invention may be prepared by using various nucleic acid synthesis techniques and instruments known to one skilled in the art (Ausubel et al., Current Protocols in Molecular Biology, Chs 2. and 4, Wiley Interscience, 1989; Maniatis, et al., Molecular Cloning: A laboratory Manual, Cold Spring Harbor Lab., New York, 1982; and U.S. Pat. Nos. 4,458,066 and 4,650,675). In addition, the CpG ODN of the present invention may be prepared from an already existing nucleic acids sequence by using a restriction enzyme, exonuclease or endonuclease.

Preferably, the CpG ODN of the present invention has a phosphodiester backbone. The phosphodiester backbone, which is a basic backbone of DNA, is degraded easily by nuclease in vivo, and, thus has little possibility for causing toxicity in vivo. The CpG ODN of the present invention is characterized by showing excellent immunoactivity in vivo as well as in vitro, unlike other CpG ODNs, even if it has a phosphodiester backbone. The CpG ODN of the present invention may have a modified backbone. It has been demonstrated that modification of an oligonucleotide backbone can enhance the activity and/or stability of the CpG ODN when administered in vivo. In the CpG ODN of the present invention, a preferred modification of the backbone includes the modification into phosphorothioate, which imparts resistance against degradation. The modification into phosphorothioate may occur at either terminus of the CpG ODN: for example, the last two or three 5' or 3' nucleotides may be linked with a phosphorothioate bond. Further, the CpG ODN of the present invention also may be modified so as to have a secondary structure (e.g. stem loop structure) such that it is resistant against degradation. Preferably, the CpG ODN may be modified to have one or more partially phosphorothioate-modified backbone. Phosphorothioate may be synthesized by way of automatic techniques using phosphoramidate or H-phosphonate chemistry (S. E. Beaucage et al., Tetrahedron Lett., 22:1859, 1981; Connolly et al., Biochemistry, 23:3443, 1984; Agrawal et al., Proc. Anti. Acad. Sci. U.S.A. 85:7079-7083, 1988; Garegg et al., Tetrahedron Lett., 27:4051-4054, 1986; Froehler et al., Nucl. Acid. Res., 14:5399-5407, Garegg et al., Tetrahedron Lett., 29:2619-2622, 1988). As another example of the modification, aryl- and alkyl-phosphonate can be prepared in a known manner, for example, as described in U.S. Pat. No. 4,469,863. In addition, alkylphosphotriester (i.e. the charged phosphonate oxygen is alkylated as set forth in U.S. Pat. No. 5,023,243 or European Patent No. 092574) can be prepared by an automatic solid phase synthesis using commercial reagent. Still another modification for reducing degradation sensitivity of the CpG ODN includes a modification of adenine, cytosine, guanine, thymine and uridine into their acetyl- and thio-derivatives or similar modifications, as well as inclusion of atypical bases such as inosine and quesine. Additionally, CpG ODNs end-capped with a diol, such as tetraethylglycol or hexaethylene glycol, are more resistant against degradation. Further, a combination of phosphodiester with phosphorothioate, phosphotriester, phosphoraminate, methyl phosphoate, methyl phosphorothionate, phosphorodithioate and combinations thereof may be used (Khorana et al., *J. Molec. Biol.*, 72:209, 1972; Reese, *Tetrahedron Lett.*, 33:3143-3179, 1978; Jaget et al., *Biochemistry.*, 27:7237, 1988; Agrawal et al., *Proc. Antl. Acad. Sci.* U.S.A. 85:7079-7083, 1988; Uhlmann, E. et. al., *Chem. Rev.*, 90:544, 1990; Goodchild, J. *Bioconjugate Chem.*; 4:165, 1990). It is believed that the CpG ODNs having a backbone modified as described above may show stronger immunological effects due to enhanced nuclease resistance, increased cellular uptake, increased protein uptake and/or altered intracellular localization.

A preferred backbone of the CpG ODN of the present invention is phosphodiester (referred to as "O type" hereinafter) or phosphorothioate (referred to as "S type" hereinafter). The most preferred backbone is the O type backbone, which is easily degraded in vivo, and thus causes no side effects.

The CpG ODN of the present invention has a physiological activity that controls the Th1/Th2 immune response balance by inhibiting a Th2 cytokine (e.g. IL-4 and IL-10) and/or by inducing a Th1 cytokine (e.g. IL-12 and IFN-γ). More particularly, the CpG ODN of the present invention activates macrophages, leucocytes and dendritic cells to induce the expression of IL-12 and/or IFN-γ. In addition, the CpG ODN of the present invention increases the expression of the surface molecules of dendritic cells (e.g. MHC class III, CD80, and CD86) in a concentration-dependent manner, and induces proliferation of both T lymphocytes and peripheral blood mononuclear cells. Further, the CpG ODN of the present invention reduces $CD4^+$ and $CD8^+$ T lymphocytes in the lesions of atopic dermatitis, and decreases the serum IgE level. Contrary to the conventional CpG ODNs known to one skilled in the art, the CpG ODN of the present invention shows almost the same activity regardless of the structure of backbone.

Therefore, the present invention provides a method for inhibiting a Th2 cytokine and/or inducing a Th1 cytokine, and for stimulating an immune response, which comprises administering the inventive CpG ODN to a subject in need thereof. The Th2 cytokine inhibited by the CpG ODN of the present invention includes all kinds of cytokines secreted in the Th2 cells. For example, the Th2 cytokine includes IL-4, IL-5, IL-10, IL-13, or the like. The Th1 cytokine induced by the CpG ODN of the present invention includes all kinds of cytokines secreted in the Th1 cells, and particular example thereof includes IL-12, IFN-γ, or the like. As used herein, "stimulating an immune response" includes activation of dendritic cells, induction of proliferation of immune cells (e.g. T lymphocytes and peripheral blood mononuclear cells), induction of inflammation-related cytokines (e.g. TNF-γ, MIP-2, IL-1, IL-12), and/or induction of recovery of immunosuppression responses caused by UV irradiation.

The CpG ODN of the present invention also has the effect of treating a skin disease or of improving a skin disease condition by virtue of the above-mentioned activities. Therefore, the CpG ODN of the present invention can be used effectively for the treatment or prevention of skin diseases. The present invention also provides a method for treating or preventing a skin disease, which comprises administering the inventive CpG ODN to a subject in need thereof. The skin diseases, to which the present invention may be applied, includes a disease caused by an imbalance in Th1/The immune responses, i.e. a skin disease caused by at least one factor selected from the group consisting of overexpression of cytokine mediated by Th2-lymphocytes; low expression of cytokine mediated by Th1-lymphocytes; an increase in the serum IgE level; abnormalities in the numbers and functions of $CD8^+$ phenotype T lymphocytes and/or $CD4^+$ phenotype T lymphocytes; and deactivation of dendritic cells and/or macrophages. More particularly, the skin disease that may be treated or prevented by the CpG ODN of the present invention includes a disease caused by low expression of a Th1 cytokine, IL-12, or a disease that may be treated by increasing expression or production of IL-12.

IL-12 serves to amplify the innate immunity generated against initial infection, as well as to induce a more effective adaptive immune response by participating in the interaction between T cells and APCs (antigen presenting cells), including dendritic cells and macrophages. The IL-12 production from APCs such as dendritic cells or macrophages is performed by two types of mechanisms, i.e. T cell-independent mechanism and T cell-dependent mechanism. The T cell-independent mechanism is induced by infectious agents including virus or bacteria, or products thereof, such as LPS or bacterial DNA (D Andrea A et al., *J. Exp. Med.*, 176:1387, 1992; Sato T et al., *Science* 273:352-354, 1996). The mechanism suggests the immunological importance of IL-12 as a mediator for linking the innate immunity with adaptive immunity. Meanwhile, the T cell-dependent IL-12 production mechanism is induced mainly by the interaction with activated T cells that provide co-stimulatory signals through molecules such as CD40 ligands (Shu U et al., *Eur. J. Immunol.*, 25:1125-1128, 1995; Cella M et al., *J. Exp. Med.*, 184: 747-752, 1996). This mechanism indicates that IL-12 plays an important role in inducing T cell immune responses, such as proliferation of cytotoxic T cells and an increase in the cytotoxicity, or continuous maintenance of Th1 immune response upon the formation of adaptive immunity. IL-12 is produced mainly from APCs, and it directly affects the dendritic cells or macrophages to induce the production of IFN-γ. Also, IL-12 may acts on the activated T cells. In this case, it induces production of IFN-γ from T cells and controls the immune response induced by IFN-γ (Chan S H et al., *J. Exp. Med.*, 173:869-879, 1991).

It is known that IL-12 is related with various diseases. Examples of such disease include: atopic dermatitis and allergic skin disease (Neumann C., et al., *J Mol Med.*, 74: 401-406, 1996; Aiba S., et al., *Exp Dermatol.*, 12: 86-95, 2003; Nilsson C., et al., *Clin Exp. Allergy.*, 34: 373-380, 2004); viral skin disease (Katakura, T., et. al., *Clin. Immunol.* 105:363-370, 2002 Hengge U. R., et al., *Br. J. Dermatol.*, 149:15-19, 2003; Arany I., et al., *Antiviral Res.*, 43: 55-63, 1999); skin cancer (Rook AH., et al *Ann. N.Y. Acad. Sci.*, 795:310-318, 1996; Gollob, J A., et al., *J. Clin. Oncol.*, 21:2564-2573, 2003; Trinchieri G., et al., *Annu Rev Immunol.*, 13: 251-276, 1995; and Krepler C., et al., *J invest Dermatol.*, 122: 387-391, 2004); or the like.

Therefore, skin disease, to which the present invention may be applied, is one caused by abnormal balance of Th1/Th2 immune responses. Particularly, the present invention may be applied for the treatment of atopic dermatitis, allergic skin disease, viral skin diseases and skin cancer.

The CpG ODN of the present invention may be administered directly to a subject. Otherwise, the CpG ODN of the present invention may be administered in the form of a nucleic acid delivery complex through the coupling with molecules inducing high-affinity bonding to a target cell (e.g. surface of dendritic cells) or through the encapsulation with such molecules. The CpG ODN of the present invention may be coupled to a sterol (e.g. cholesterol), lipid (e.g. cationic lipid, virosome or liposome) or a target cell-specific coupling agent (e.g. ligand recognized by target cell-specific receptor) via ionic bond or covalent bond. Examples of a suitable coupling agents or cross-linking agents include protein A, carbodiimide, N-succinimidyl-3-(2-pyridyldithio) propionate (SPDP), or the like.

The CpG ODN of the present invention may be administered via various routes in a manner known to one skilled in the art (Donnelly et al., *J. Imm. Methods.*, 176:145, 1994; Vitrello et al., *J. Clin. Invest.*, 95:341, 1995). In other words, the CpG ODN according to the present invention may be administered via an oral or a parenteral route, for example, via an oral, intramuscular, intravenous, intradermal, intraarterial, intramedullar, intradural, intraperitoneal, intranasal, intravaginal, rectal, sublingual or subcutaneous route, or via a gastrointestinal tract, a mucous membrane or a respiratory organ. For example, the CpG ODN of the present invention may be formulated into a formulation for injection, which is injected into a subcutaneous layer at a given amount by using a 30 gauge injection needle. Otherwise, such formulations for injection may be as ministered by lightly pricking the skin with 30 gauge injection needle, or may be applied directly onto the skin.

In addition, the CpG ODN of the present invention may be formulated into various forms for oral or parenteral administration by conventional methods known to one skilled in the art. In the case of an oral formulation, the CpG ODN of the present invention may be mixed with vehicles, so as to be formulated into oral tablet, buccal tablet, troche, capsule, elixir, suspension, syrup and wafer. Such formulations may further comprise, in addition to the active ingredient, diluents (e.g. lactose, dextrose, sucrose, mannitol, sorbitol, cellulose and/or glycine) and surfactants (e.g. silica, talc, stearic acid, magnesium or calcium salt thereof and/or polyethylene glycol). The tablet may comprise a binder, such as magnesium aluminum silicate, starch paste, gelatin, tragacanth, methyl cellulose, sodium carboxymethyl cellulose and/or polyvinyl pyrrolidone. If desired, the tablet may further comprise a disintegrating agent such as starch, agar, alginic acid or sodium salt thereof, an absorbent, a colorant, a flavoring agent and/or a sweetening agent. Such formulations may be prepared by conventional mixing, granulation or coating processes.

Additionally, the formulations for parenteral administration include a injection formulation, such as isotonic aqueous solution or suspension, or a formulation for skin application. The injection formulation may be prepared by using suitable dispersing or wetting agents, and suspending agents, according to any technique known in the art. For example, the formulation for injection may be prepared by dissolving each ingredient in a saline or buffer solution. The formulation for skin application may be prepared by mixing the pharmaceutical composition according to the present invention with pharmaceutically acceptable carriers, and formulating the mixture in the form of powder, liniment, gel, lotion, cream, ointment, pasta, puff, aerosol, suppository, or the like. Among these formulations, ointment is particularly preferred. The carrier that may be used in each formulation includes: hydrocarbons such as vaseline, liquid paraffin, gelled hydrocarbon, or the like; animal or vegetable oil such as heavy chain fatty acid triglyceride, pig fat, hard fat, cacao oil, or the like; higher fatty acid alcohols and esters thereof such as cetanol, stearyl alcohol, stearic acid, isopropyl palmitate, or the like; water-soluble bases such as polyethylene glycol, 1,3-butypene glycol, glycerol, gelatin, white sugar, sugar alcohols, or the like; emulsified acrylates such as glycerin fatty acid ester, polyoxy stearate, polyoxyethylene cured castor oil, or the like; adhesives such as acrylic acid ester, sodium alginate, or the like; and spraying agents such as liquefied petroleum gas, carbon dioxide, or the like; and preservatives such as paraoxy benzoate. The formulations according to the present invention may further comprise stabilizers and preservatives. Suitable stabilizers include antioxidants, such as sodium bisulfite, sodium sulfite or ascorbic acid. Suitable preservatives include benzalkonium chloride, methyl- or propyl-paraben, and chlorobutanol. For other pharmaceutically acceptable carriers, reference may be made to the following literature: Remington's Pharmaceutical Sciences, 19th ed., Mack Publishing Company, Easton, Pa., 1995.

The total effective amount of the CpG ODN of the present invention may be administered to a patient in a single dose, or by a fractionated treatment protocol with multiple doses over a longer period. The pharmaceutical composition comprising the CpG ODN of the present invention may have different amounts of the active ingredient depending on the severity of a disease. In the case of systemic administration, the pharmaceutical composition according to the present invention may be administered preferably as a daily dose sufficient for obtaining a concentration of the oligonucleotide in the blood of about 0.01 μM to 100 mM. In the case of local administration, a smaller dose of the active ingredient may be administered compared to administration via other routes. Preferably, the total dose of the CpG ODN of the present invention ranges from about 0.01 μg to 100 mg per kg of the body weight per day. However, the concentration of the CpG ODN is determined according to various factors including an administration route, treatment frequency, the age, body weight, condition, sex, disease severity, dietary condition and excretion state of a patient. Therefore, considering the above factors, effective amount of the CpG ODN for use in treating or preventing a skin disease may be determined with ease by' one skilled in the art. However, the pharmaceutical composition according to the present invention is not limited to the above formulations, administration routes and administration methods, as long as it shows desired effects of the present invention. The pharmaceutical composition according to the present invention may be administered alone, or in combination with other therapies known to one skilled in the art, including chemotherapy, radiotherapy, a surgical operation, other oral treating agents and ointments (e.g. Elidel, pimecrolimus). Also, the inventive pharmaceutical composition may be administered in combination with other immunoadjuvants known to one skilled in the art. The immunoadjuvants that may be used include INF-γ, IL-12, cyclosporine, FK506 (Tacrolimus), TP-5 (Thymopoietin pentapeptide, thymopentin), or the like. If necessary, the pharmaceutical composition comprising the CpG OND according to the present invention may further comprise at least one selected from the group consisting of: antibiotics including tetracycline, oxytetracycline, gentamicin, neomycin sulfate, bacitracin, polymyxin B sulfate and mupirocin; anti-histamines including diphenhydramine, prometadine, triperenamin, phenothiazine, chloropeniramin, anthazoline and phantholyl; anti-inflammatory drugs; anti-viral agents; and anti-fungal agents.

BRIEF DESCRIPTION OF THE DRAWINGS

The foregoing and other objects, features and advantages of the present invention will become more apparent from the following detailed description when taken in conjunction with the accompanying drawings in which.

Control: non-treated.

Figure 3:
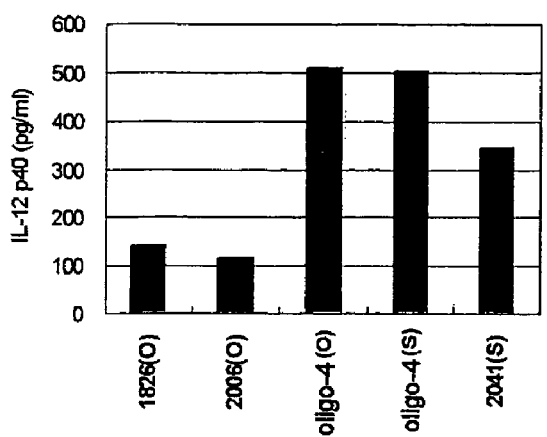
Figure 3:
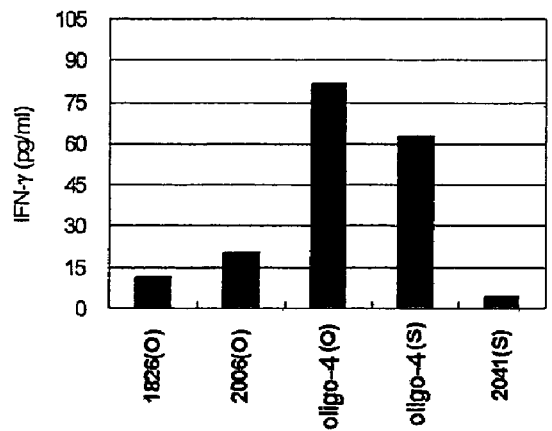

FIG. 3 shows the effect of the backbone modification in the oligo-4 CpG ODN of the present invention upon the production of IL-12 p40 (A) and IFN-γ (B), as compared to CpG ODNs (1826 and 2006) according to the prior art and non-CpG ODN (2041).

Figure 4:
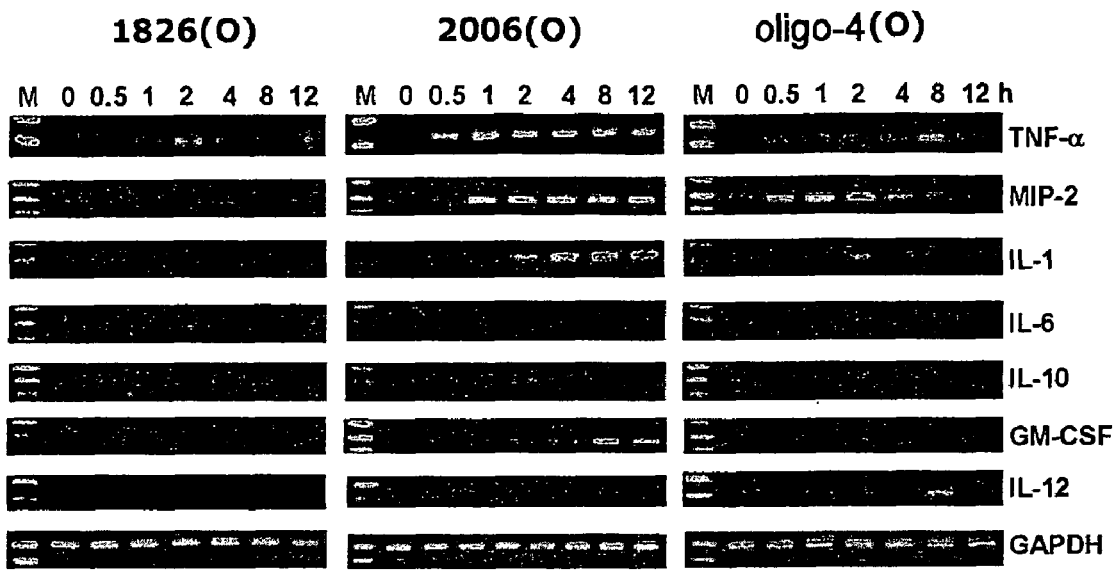

FIG. 4 shows the effect of the O-type oligo-4 CpG ODN of the present invention upon the expression of inflammation-related cytokines in macrophages, as compared to O-type CpG ODNs (1826 and 2006) according to the prior art.

Figure 5:
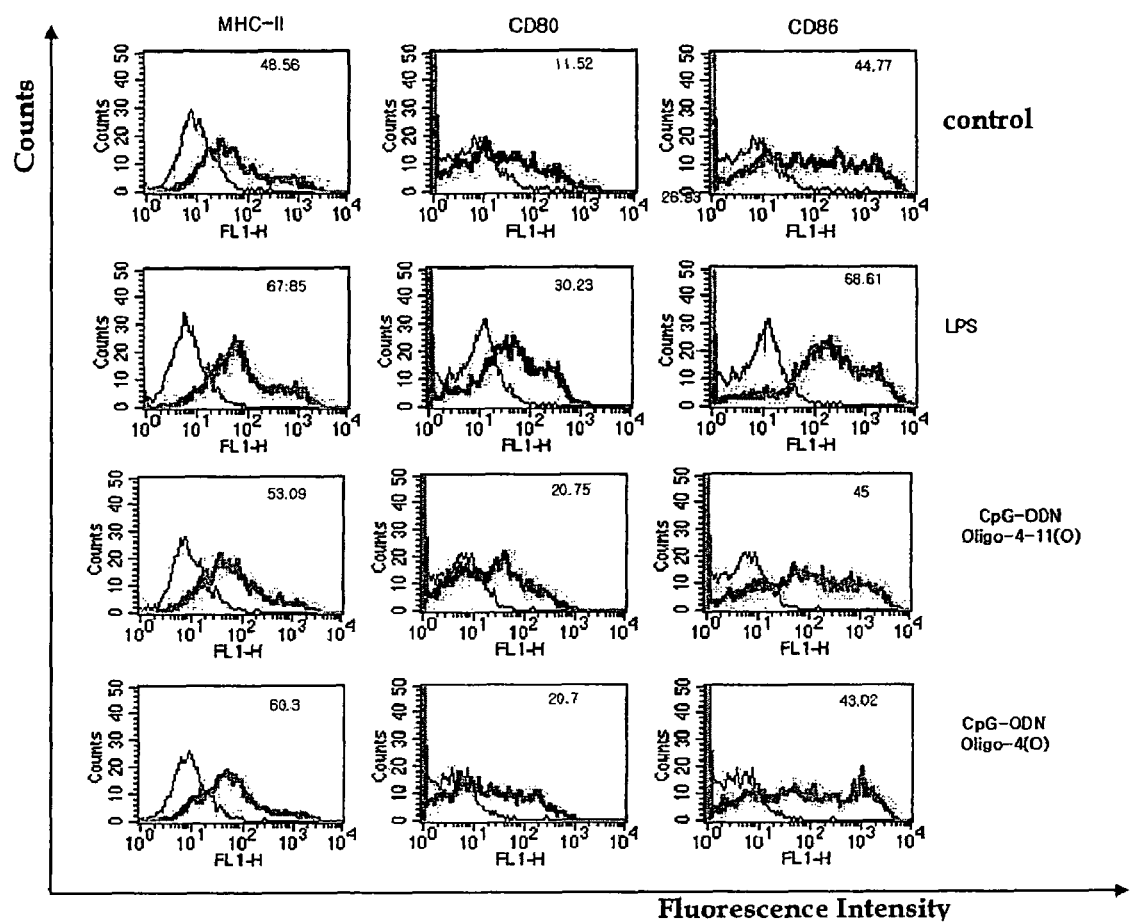

FIG. 5 shows the effect of the O-type CpG ODNs according to the present invention upon the activation of the cell surface molecules (MHC-11, CD80 and CD86) of dendritic cells.

Control: non-treated.

LPS: treated with lipopolysaccharide (positive control).

Figure 6:
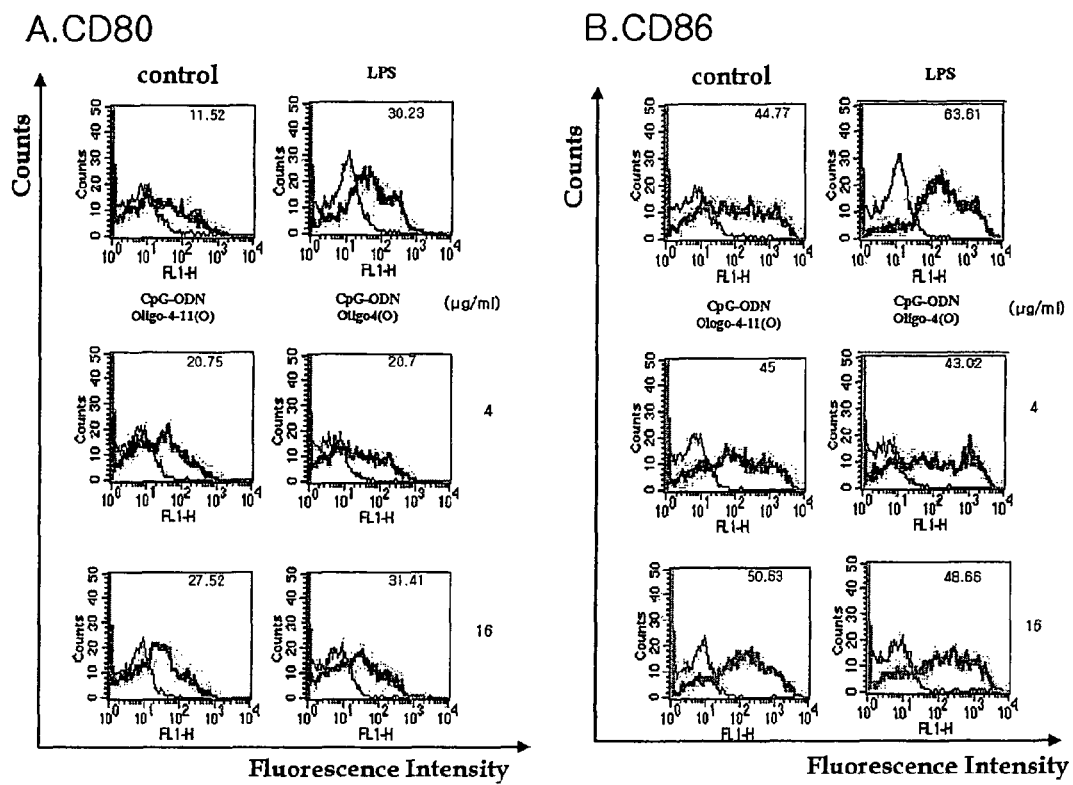

FIG. 6 shows the effect of the O-type CpG ODNs according to the present invention according to their concentration upon the activation of the cell surface molecules (CD80 and CD86) of dendritic cells.

Control: non-treated.

LPS: treated with lipopolysaccharide (positive control).

Figure 7:

FIG. 7 shows the effect of the O-type oligo-4 CpG ODN according to the present invention upon the expression of IL-12 in dendritic cells, as compared to O-type 1826 CpG ODN according to the prior art and non-CpG ODN (2041).

Figure 8:
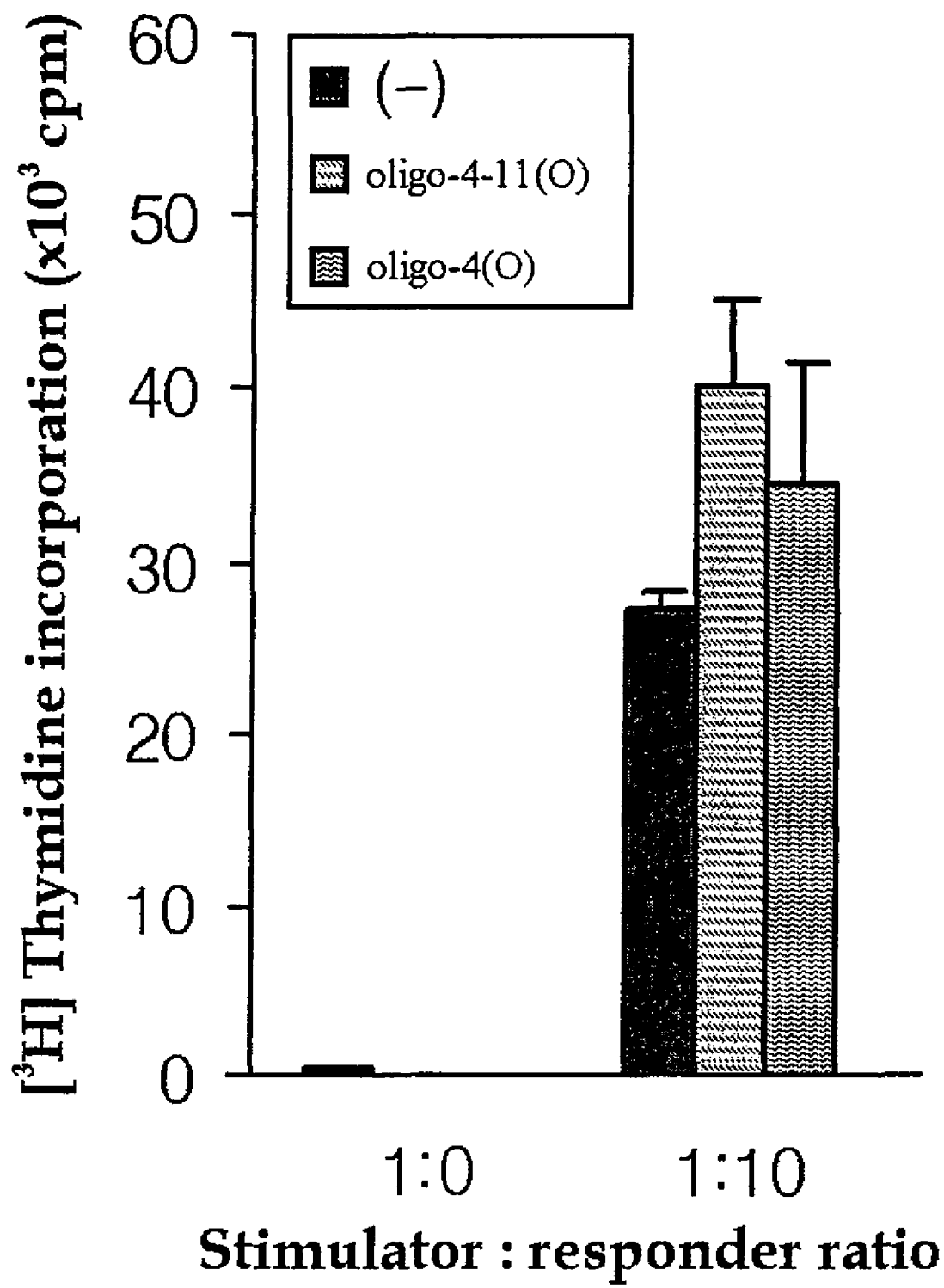

FIG. 8 shows the effect of the O-type CpG ODNs (oligo-4-11 and oligo-4) of the present invention upon the proliferation of allogenic T lymphocytes.

Figure 9:
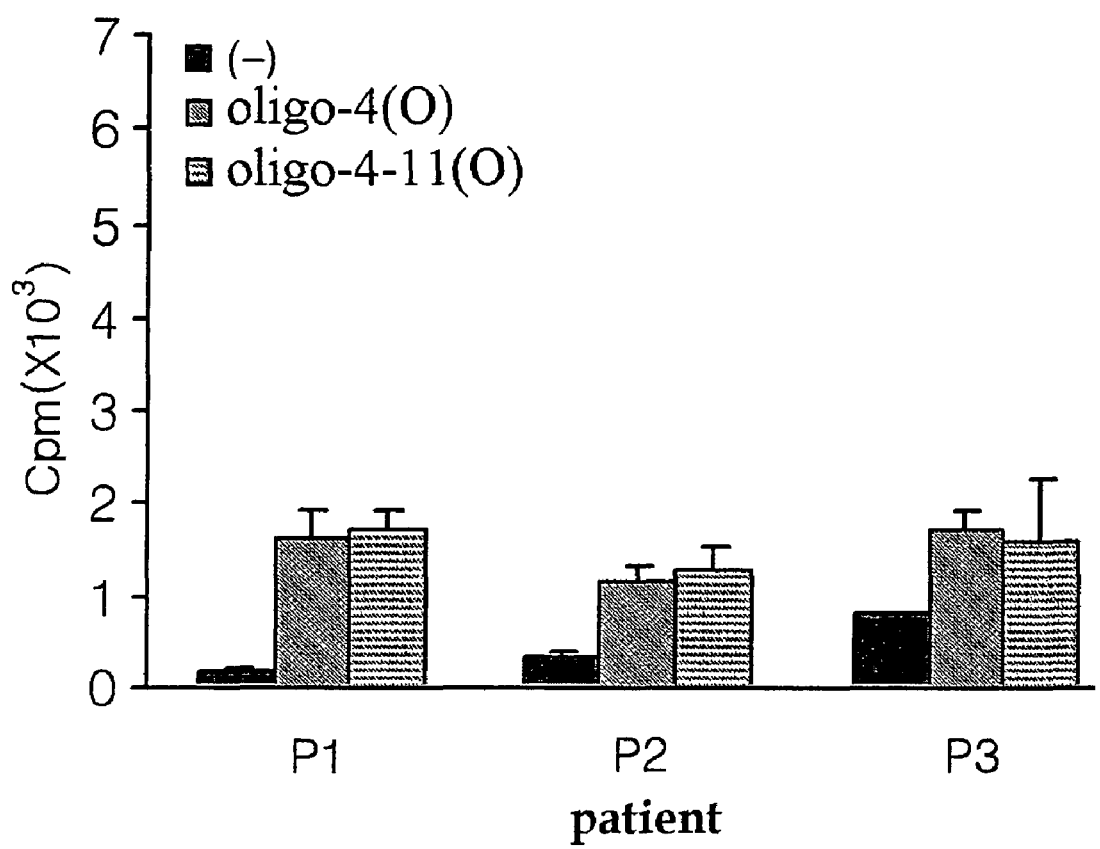

FIG. 9 shows the effect of the O-type CpG ODNs (oligo-4-11 and oligo-4) upon the proliferation of peripheral blood mononuclear cells (PBMC).

Figure 10:
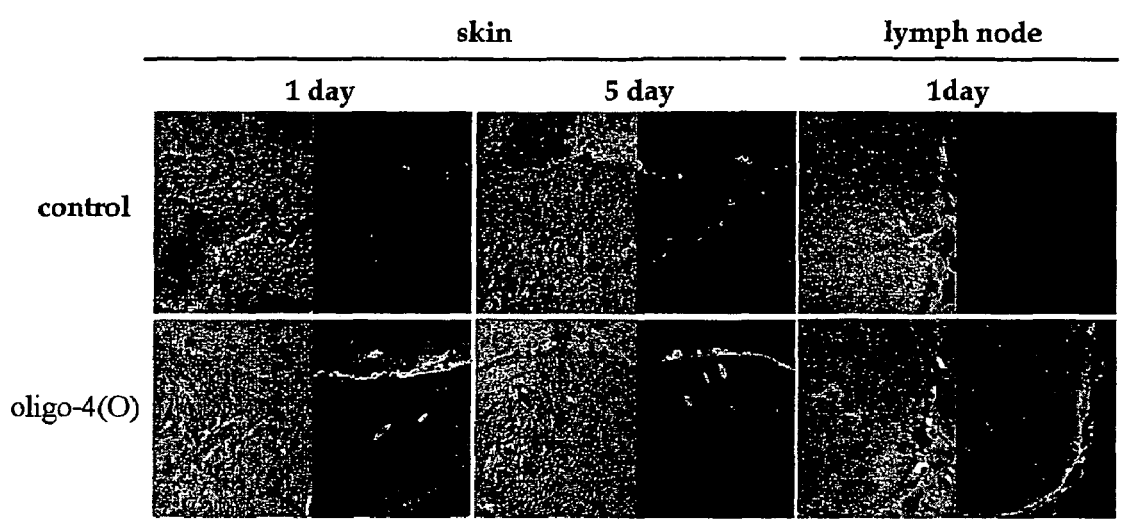

FIG. 10 is a photograph that shows the infiltration of inventive O-type oligo-4 CpG ODN labeled with FITC into the epidermis of the back of an NC/Nga mouse.

Figure 11:
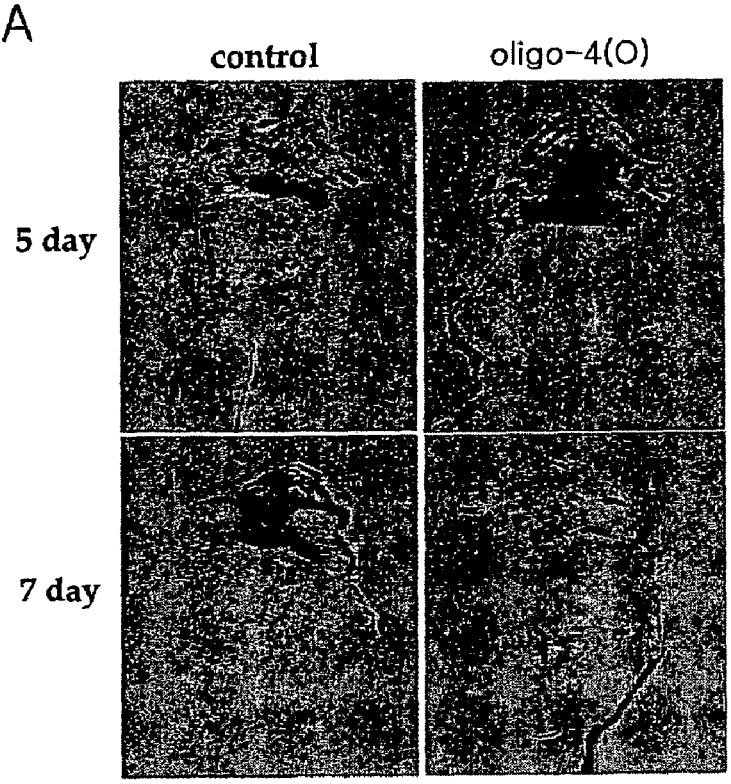
Figure 11:
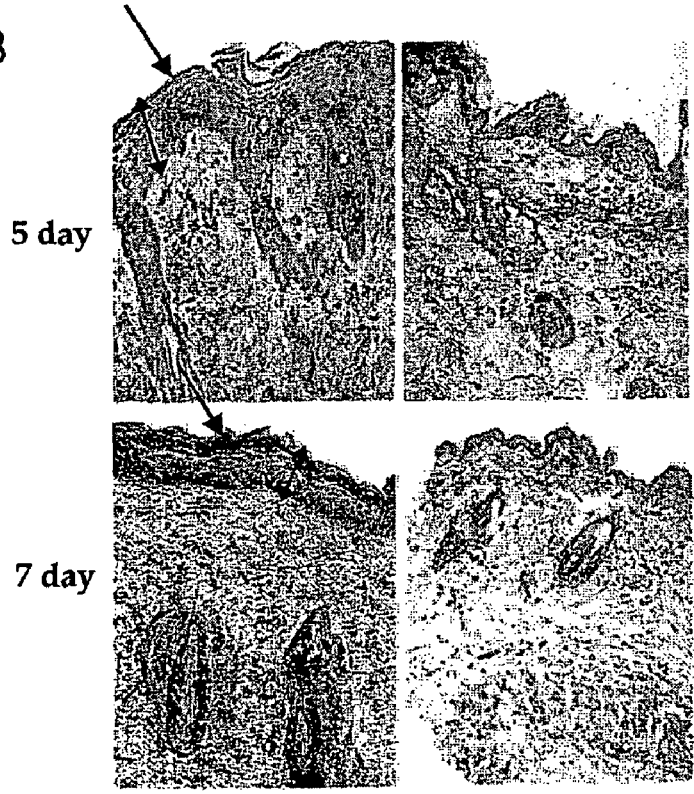

FIG. 11 shows the results for the treatment of atopic dermatitis by the administration of the O-type oligo-4 CpG ODN of the present invention, in an animal model.

A: photographs taken on the fifth day and seventh day after application of the O-type oligo-4 CpG ODN of the present invention onto an atopic dermatitis lesion on the back of an NC/Nga mouse, which is observed with the naked eye.

B: photographs taken by removing the skin after applying the O-type oligo-4 CpG ODN of the present invention onto the back skin of an NC/Nga mouse suffering from atopic dermatitis, and then subjecting the skin to H&E staining.

⇆: acanthosis

→: hyperkeratosis

Figure 12:
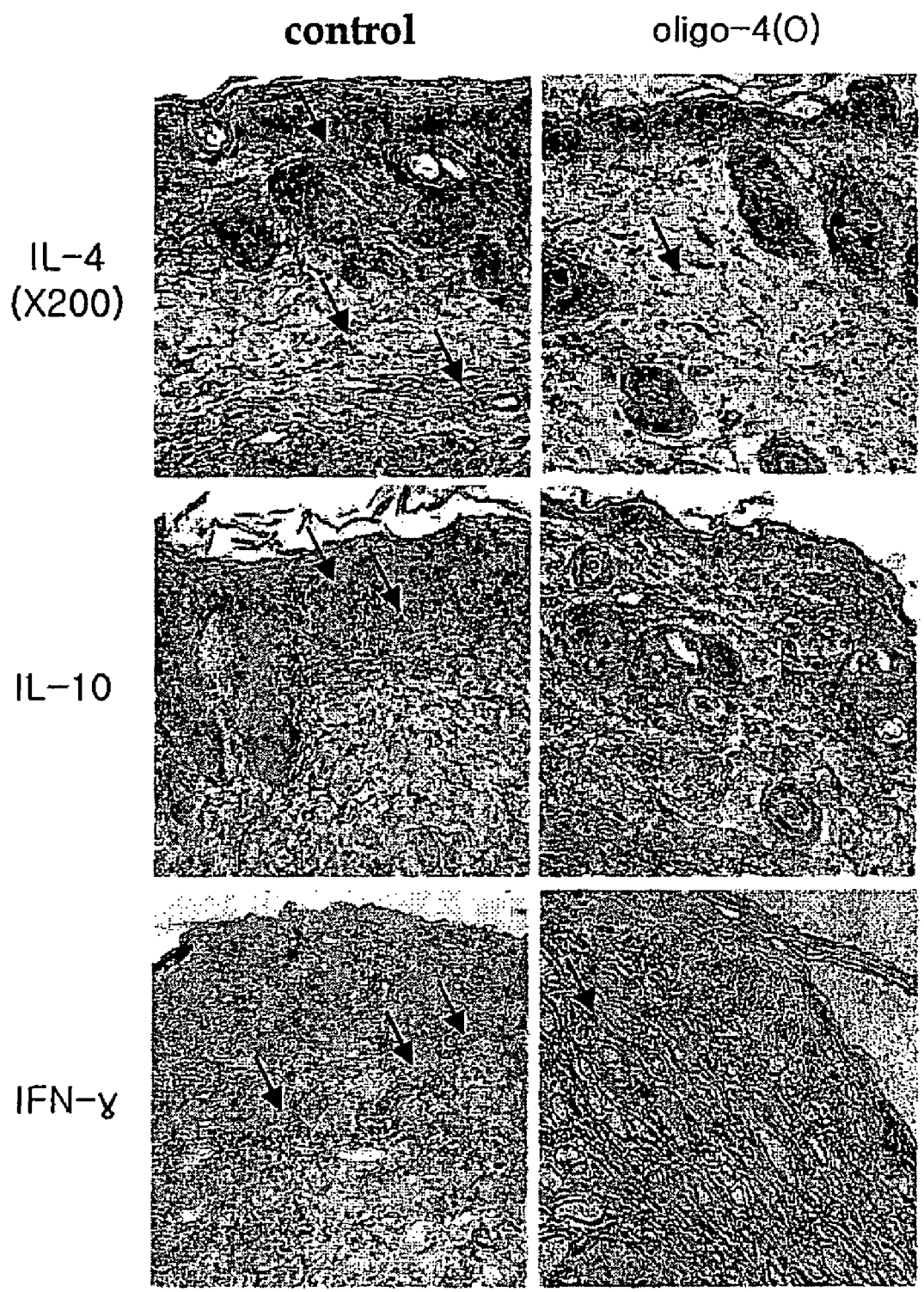

FIG. 12 shows the results of the immunohistochemistry for the expression of cytokines (IL-4, IL-10 and IFN-γ) in the back skin of an NC/Nga mouse, to which the O-type oligo-4 CpG ODN of the present invention is administered. The arrow mark represents the expression of cytokines.

Figure 13:
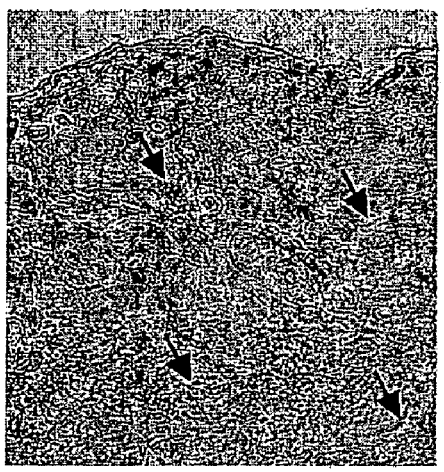
Figure 13:
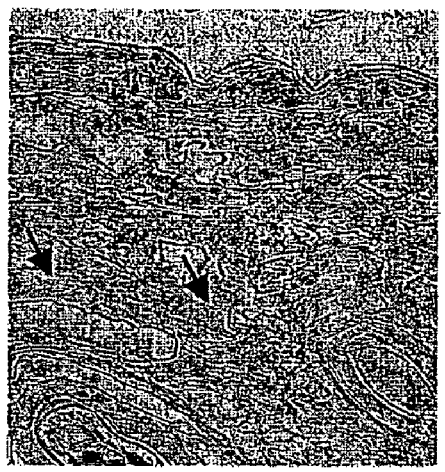

FIG. 13 shows the results of the immunohistochemistry for the infiltrated CD4[+] and CD8[+] lymphocytes, before and after the treatment, in the back skin of an NC/Nga mouse to which the O-type oligo-4 CpG ODN of the present invention is administered. The arrow mark represents CD4[+] and CD8[+] lymphocytes.

Figure 14:
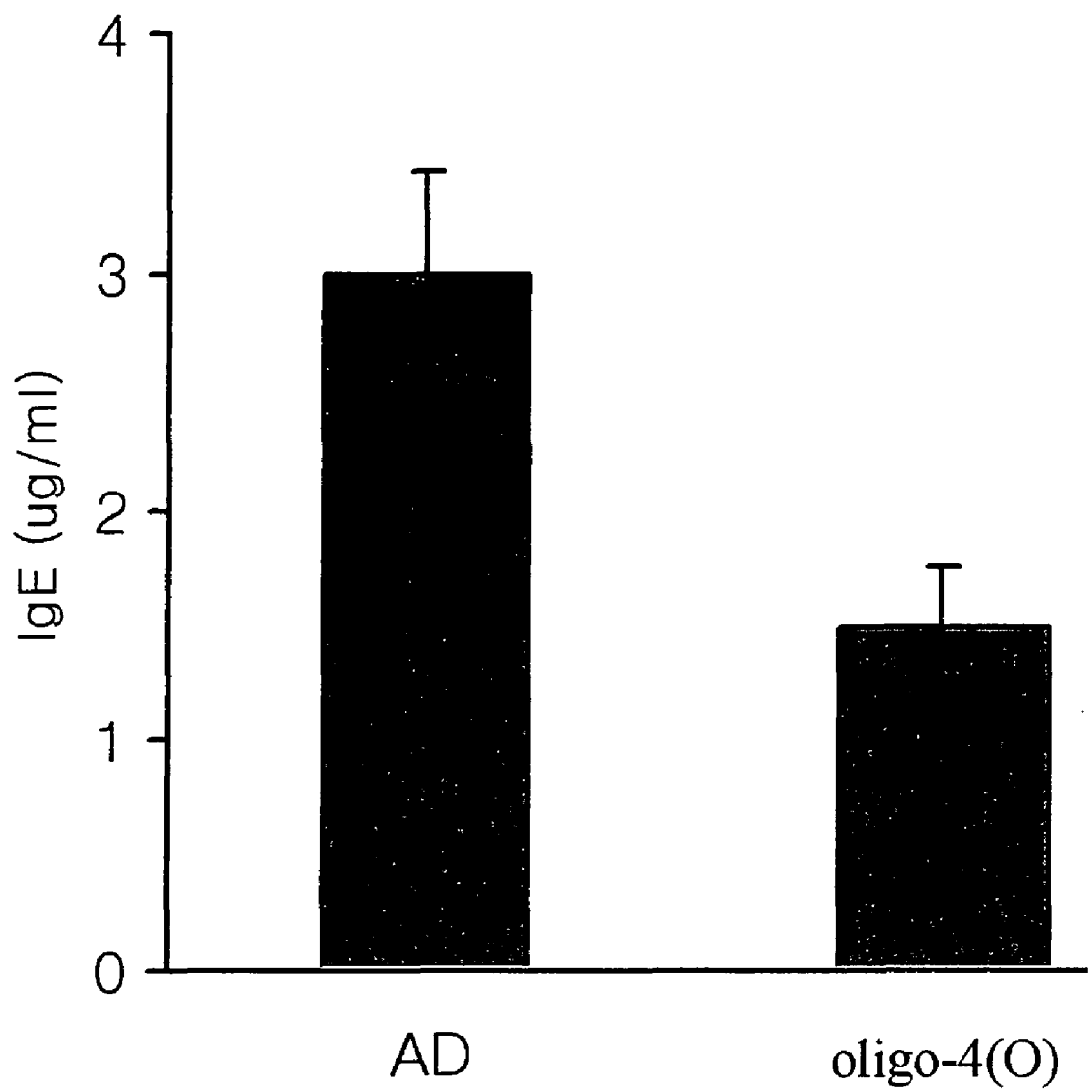

FIG. 14 shows the results for the serum IgE level in an NC/Nga mouse, after administering the O-type oligo-4 CpG ODN of the present invention.

AD: non-treated control.

Figure 15:
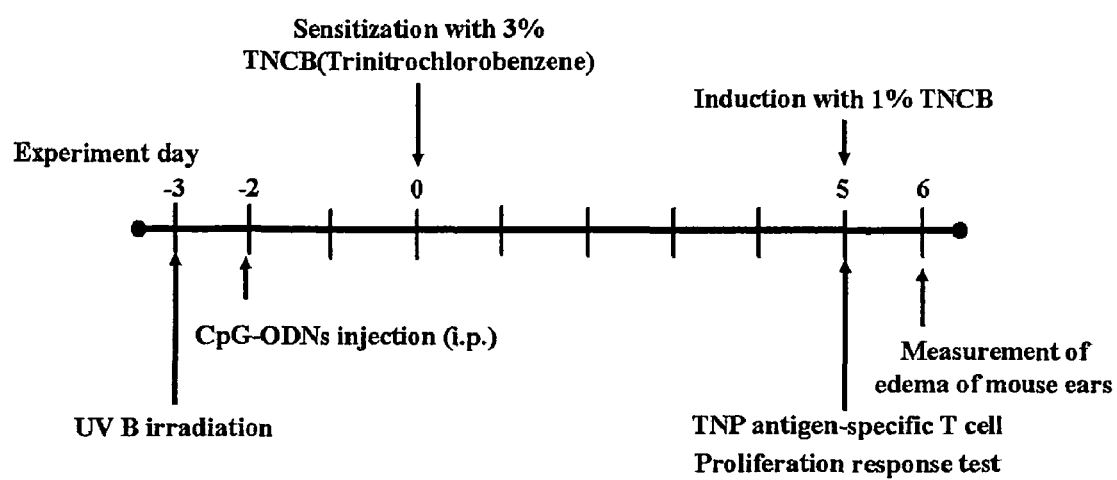

FIG. 15 shows the experimental procedure for demonstrating the recovery effect Of contact hypersensitivity by the CpG ODN of the present invention, in opposition to the inhibition of contact hypersensitivity caused by UV irradiation in a mouse.

Figure 16:
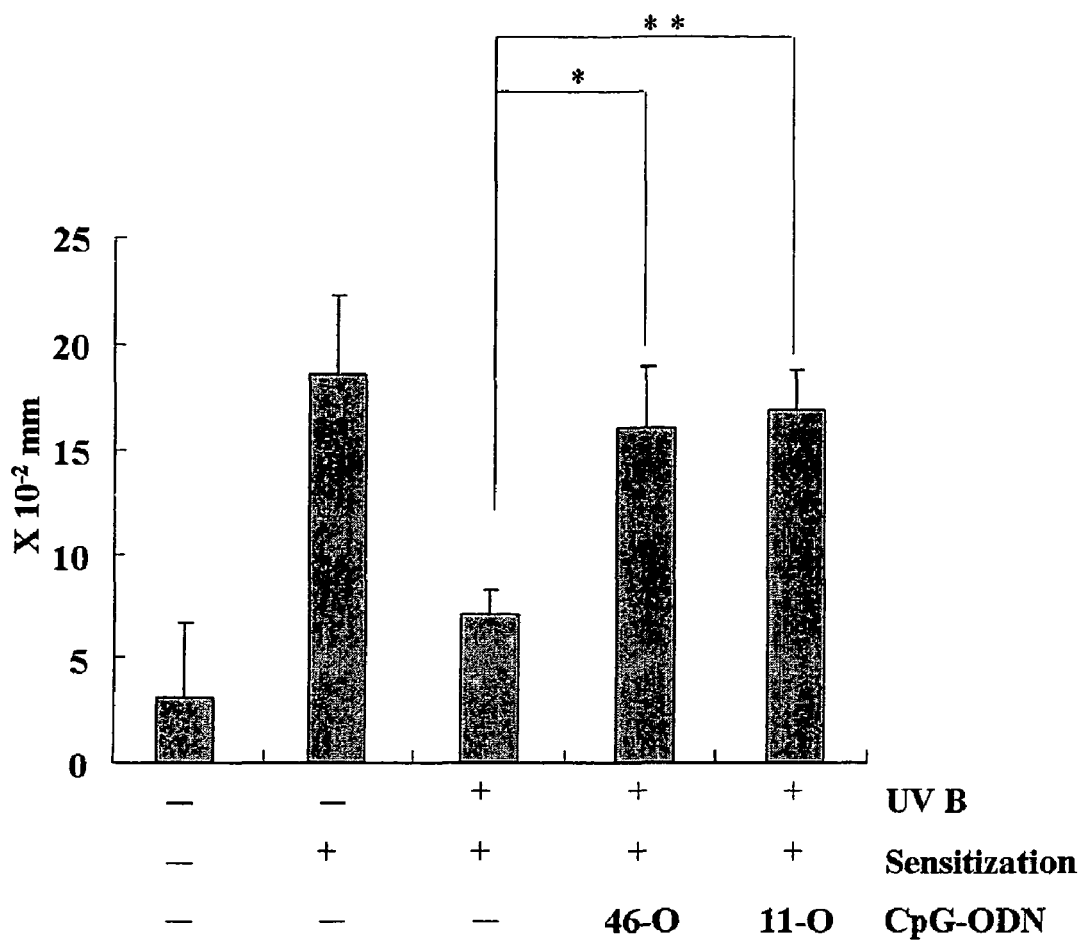

FIG. 16 shows the recovery effect, of contact hypersensitivity by the CpG ODN of the present invention, in opposition to the inhibition of contact hypersensitivity causes by UV irradiation in a mouse. * means p<0.05, and ** means p<0.01.

Figure 17:
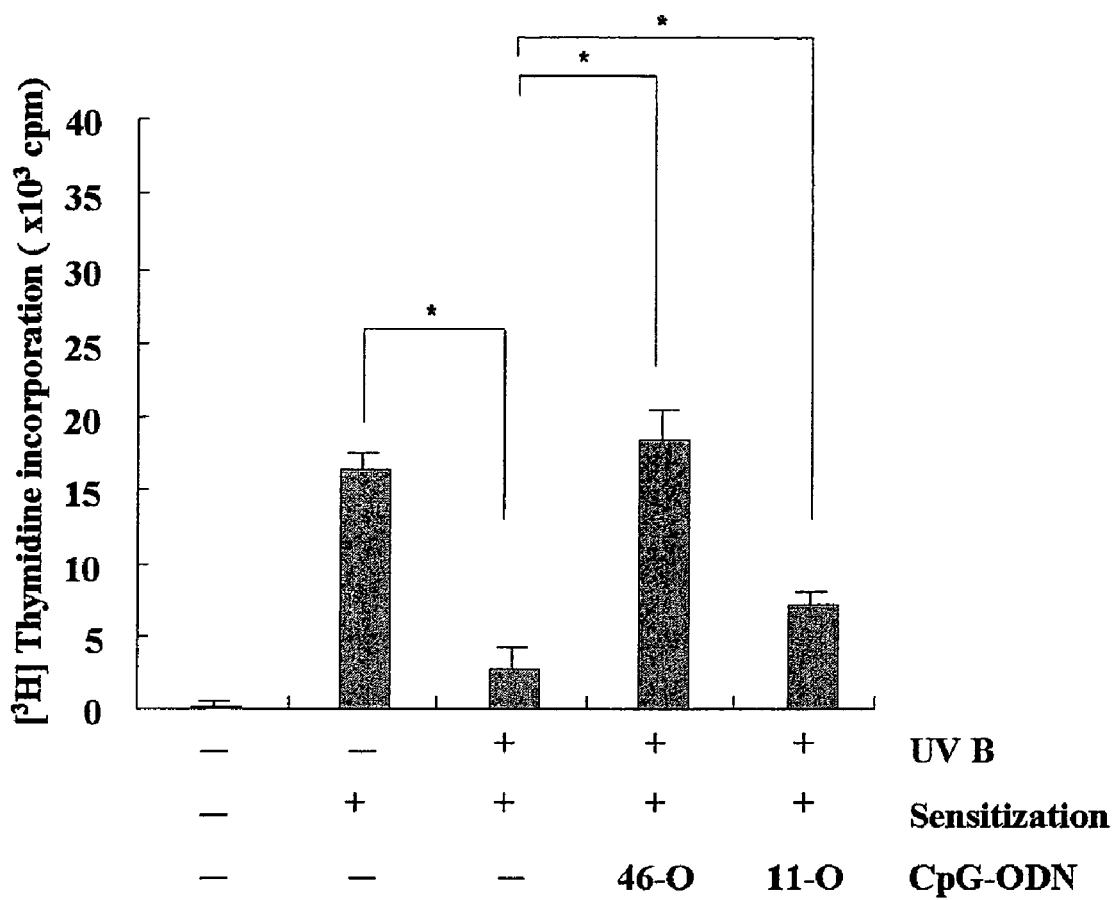

FIG. 17 shows the effect of the CpG ODN of the present invention upon the induction of proliferation responses of T cells isolated from the spleen of a mouse in which contact hypersensitivity is inhibited by UV irradiation. * means p<0.05.

BEST MODE FOR CARRYING OUT THE INVENTION

Reference will now be made in detail to the preferred embodiments of the present invention. It is to be understood that the following examples are illustrative only and the present invention is not limited thereto.

Example 1

Effect of Base Modification of Oligo-4 CpG ODN Upon Immune Responses

<1-1> Isolation of Oligo-4 CpG ODN and Base Modification Thereof

A CpG ODN (referred to as "oligo-4 CpG ODN" hereinafter) having the nucleotide sequence represented by SEQ ID NO. 2, which induces immune responses to a high level, was isolated from an *E. coli* chromosomal DNA fragment partially cleaved by DNase I. Next, various mutants were prepared by modifying the nucleotide sequence of the oligo-4 CpG ODN, and tested to determine immune responses thereof. Base modification of the oligo-4 CpG ODN was performed as follows: The second CpG motif from the 5'-end in the nucleotide sequence of the oligo-4 CpG ODN (SEQ ID NO. 2) was substituted with CA and CT dinucleotides, and the resultant ODNs were designated as "oligo-4-1" and "oligo-4-2", respectively. Also, the third CpG motif from the 5'-end in the nucleotide sequence of the oligo-4 CpG ODN (SEQ ID NO. 2) was substituted with TG and CA dinucleotides, and the resultant ODNs were designated as "oligo-4-3" and "oligo-4-4", respectively. Next, the dinucleotide (TT) present at the 3'-end of the second CpG motif from the tetranucleotide (TTGC) between the second CpG motif and the third CpG motif in the nucleotide sequence of the oligo-4 CpG ODN was substituted with at least one dinucleotide selected from the group consisting of AA, CC and GG, and the resultant ODNs were designated as "oligo-4-5", "oligo-4-6" and "oligo-4-7", respectively. Further, the dinucleotide (GC) present at the 5'-end of the third CpG motif from the above-mentioned tetranucleotide (TTGC) was substituted with one selected from the group consisting of GA, GT and CG, and the resultant ODNs were designated as "oligo-4-8", "oligo-4-9" and "oligo-4-10", respectively. Finally, the dinucleotide (CT) present at the side of the 5'-end of the first CpG motif; the first CpG motif (CG); the dinucleotide (CA) present between the first CpG motif and the second CpG motif; the dinucleotide (GC) present at the 5'-end of the third CpG motif; and the second and third nucleotide (AC) from the hexanucleotide (AACTTC) present at the 3'-end of the third CpG motif, in the nucleotide sequence of the oligo-4 CpG ODN, were individually substituted with GC, TC, GA, GG and TA, and the resultant ODN was designated as "oligo-4-11". Each ODN was synthesized by Genotech Co., Ltd. All of the synthesized ODNs are phosphodiester type oligonucleotides. Information about the sequence of each substitution mutant is shown in the following Table 1. In Table 1, each part expressed in a block represents a CpG motif and each underlined section indicates a modified part.

TABLE 1

Base Modification of Oligo-4 CpG ODN

| ODNs | nucleotide sequence | SEQ ID No. |
|---|---|---|
| oligo-4 | 5'-CTCGCACGTTGCCGAACTTC-3' | 2 |
| oligo-4-1 | 5'-CTCGCACATTGCCGAACTTC-3' | 9 |
| oligo-4-2 | 5'-CTCGCACTTTGCCGAACTTC-3' | 10 |
| oligo-4-3 | 5'-CTCGCACGTTGCTGAACTTC-3' | 3 |
| oligo-4-4 | 5'-CTCGCACGTTGCCAAACTTC-3' | 4 |
| oligo-4-5 | 5'-CTCGCACGAAGCCGAACTTC-3' | 11 |
| oligo-4-6 | 5'-CTCGCACGCCGCCGAACTTC-3' | 12 |
| oligo-4-7 | 5'-CTCGCACGGGGCCGAACTTC-3' | 13 |
| oligo-4-8 | 5'-CTCGCACGTTGACGAACTTC-3' | 5 |
| oligo-4-9 | 5'-CTCGCACGTTGTCGAACTTC-3' | 6 |
| oligo-4-10 | 5'-CTCGCACGTTCGCGAACTTC-3' | 7 |
| oligo-4-11 | 5'-GCTCGACGTTGGCGATACTC-3' | 8 |

<1-2> Determination of Effect of Base Modification of Oligo-4 CpG ODN Upon Immune Responses The oligo-4 CpG ODN and various substitution mutants thereof prepared in the Example <1-1> were determined for their effects upon the activation of IL-8 and IL-12 promoters of macrophages.

a) Culture of Mouse Macrophages

Raw 264.7 cells (ATCC, Manassas, Va.) were cultured in a DMEM medium containing 10% FBS (Gibco BRL). The cells were cultured in an incubator (Form a) at 37 t under 5% $CO_2$. During the culture of the cells, cell survival ratio and cell counts were measured periodically by using a hematocytometer according to the trypan blue exclusion method. The cell survival ratio was maintained to at lest 95% over the total culture period.

b) Construction of IL-8/IL-12 Promoter-Luc Reporter Plasmid

To amplify the IL-8 promoter region, PCR (polymerase chain reaction) was performed by using the human genome DNA as a template and a set of primers represented by SEQ ID NOs. 14 and 15. The amplified fragment of the IL-8 promoter region was inserted into the pGL3-Basic plasmid (Promega) cleaved by BglII and HindIII, thereby constructing IL-8 promoter-Luc reporter plasmid (Wu G. D. et al., *J. Biol. Chem.*, 272: 2396-2403, 1997).

Meanwhile, in order to amplify the IL-12 promoter region, PCR was performed by using the human genome DNA as a template and a set of primers represented by SEQ ID NOs. 16 and 17. The amplified fragment of the IL-12 promoter region was inserted into the pGL3-Basic plasmid (Promega) cleaved by Sac I and Xho I, thereby constructing IL-12 promoter-Luc reporter plasmid (Wu G. D. et al., *J. Biol. Chem.*, 272: 2396-2403, 1997).

c) Analysis for Activation of Promoters: Luciferase Activity Assay

Raw 264.7 cells (ATCC, Rockviller, MID) were plated at a concentration of $5 \times 10^4$ cells/well in 12-well plate. Next, the cells were cultured in an incubator at 37° C. under 5% $CO_2$ for 24 hours. The cells were co-transfected with the IL-8 promoter-Luc reporter plasmid or IL-12 promoter-Luc reporter plasmid, obtained as described in the above part b), as well as pRL-null plasmid (Promega). Next, the cells were cultured in an incubator at 37° C. under 5% $CO_2$ for 24 hours. The CpG ODNs described in the above Table 1 were treated to each well (10 μg/well), followed by culture in an incubator at 37 t under 5% $CO_2$ for 6 hours or 12 hours. The control was treated with PBS. After the completion of the culture, the culture solution was removed. Then, PLB (passive lysis buffer) of the Dual-luciferase reporter assay system available from Promega was added to each well to a concentration of 100 μl/well to perform the lysis of cells. The cell lysate was centrifuged and the supernatant (15 μl) was used to perform the luciferase assay. Luciferase activity was measured by using the TD-20/20 luminometer (Turner designs). The activity of each promoter after the treatment with CpG ODN was expressed in terms of the relative activity based on the control. In other words, the promoter activity was expressed by the fold activation to the activity of the control, wherein the activity of the control is taken as 1.

Figure 1:
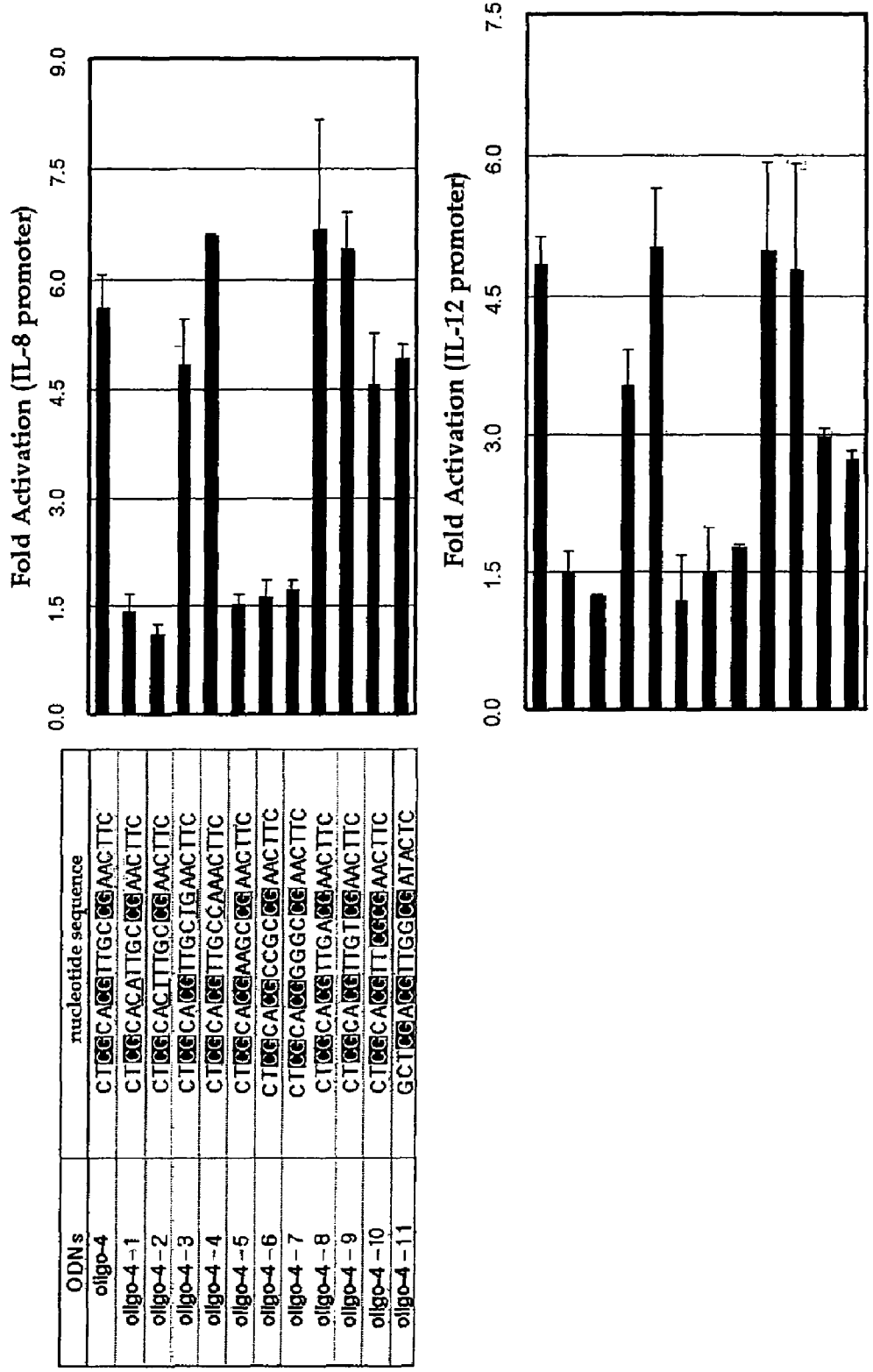
FIG. 1 shows the effect of the base modification in the oligo-4 CpG ODN of the present invention upon the activation of IL-8 promoter and IL-12 promoter.

As a result of the experiment, as shown in FIG. 1, activation patterns of the IL-8 promoter and IL-12 promoter were very similar. The mutants (oligo-4-3 and oligo-4-4), in which the third CpG motif of the nucleotide sequence in the oligo-4 CpG ODN was modified, and the mutants (oligo-4-8, oligo-4-9 and oligo-4-10), in which the bases present at the 5'-end of the above CpG motif were modified, showed high activities.

More particularly, oligo-4-4, oligo-4-8 and oligo-4-9 ODNs showed higher activities compared to oligo-4 CpG ODN. Among these, oligo-4-8 ODN showed the highest activity. Additionally, oligo-4-3 and oligo-4-10 ODNs showed relatively high activities, although they provided lower activities compared to oligo-4 CpG ODN. On the other hand, the mutants (oligo-4-1 and oligo-4-2), in which the second CpG motif sequence was modified, and the mutants (oligo-4-5, oligo-4-6 and oligo-4-7), in which the dinucleotide sequence present at the 3'-end of the second CpG motif was modified, showed significantly decreased IL-8 promoter activities. Moreover, the mutant (oligo-4-11), in which almost all bases were modified except the second CpG motifs and dinucleotide at the 3' end thereof, and the third CpG motif, showed high activity. The above results indicates that the second CpG motif and two bases present at the 3'-end of the second CpG motif in the nucleotide sequence of the oligo-4 CpG ODN is closely related with the activation of IL-promoter and IL-12 promoter.

The oligo-4 CpG ODN, which is the parent of the substitution mutants of CpG ODNs described in the above Table 1, and the oligo-4-11 CpG ODN, which undergoes modification in the nucleotide sequence to the highest level, were used to perform the following experiment.

Example 2

Effect of Backbone Modification of Oligo-4 CpG ODN Upon Immune Responses

<2-1> Assay for Activation of IL-8 Promoter

Raw 264.7 Cells were Co-Transfected with Both the IL-8 Promoter-Luc promoter reporter vector, constructed as described in the above part b) of Example 1-2, and pRL-null plasmid (Promega). The transfected cells were treated with O-type (phosphodiester backbone) and S-type (phosphorothioate backbone) oligo-4 CpG ODN (0 or 10 µg/ml), respectively, and then cultured for 8 hours. Additionally, O-type 1826 ODN (SEQ ID NO. 18) and O-type 2006 ODN (SEQ. ID NO. 19) were used as control CpG ODNs in order to compare their activities with the activity of the oligo-4 CpG ODN of the present invention. Also, as a non-CpG ODN, S-type 2041 ODN (SEQ ID NO. 20) was used. Next, activity of the IL-8 promoter was measured in the same manner as described in Example <1-2>.

Figure 2:
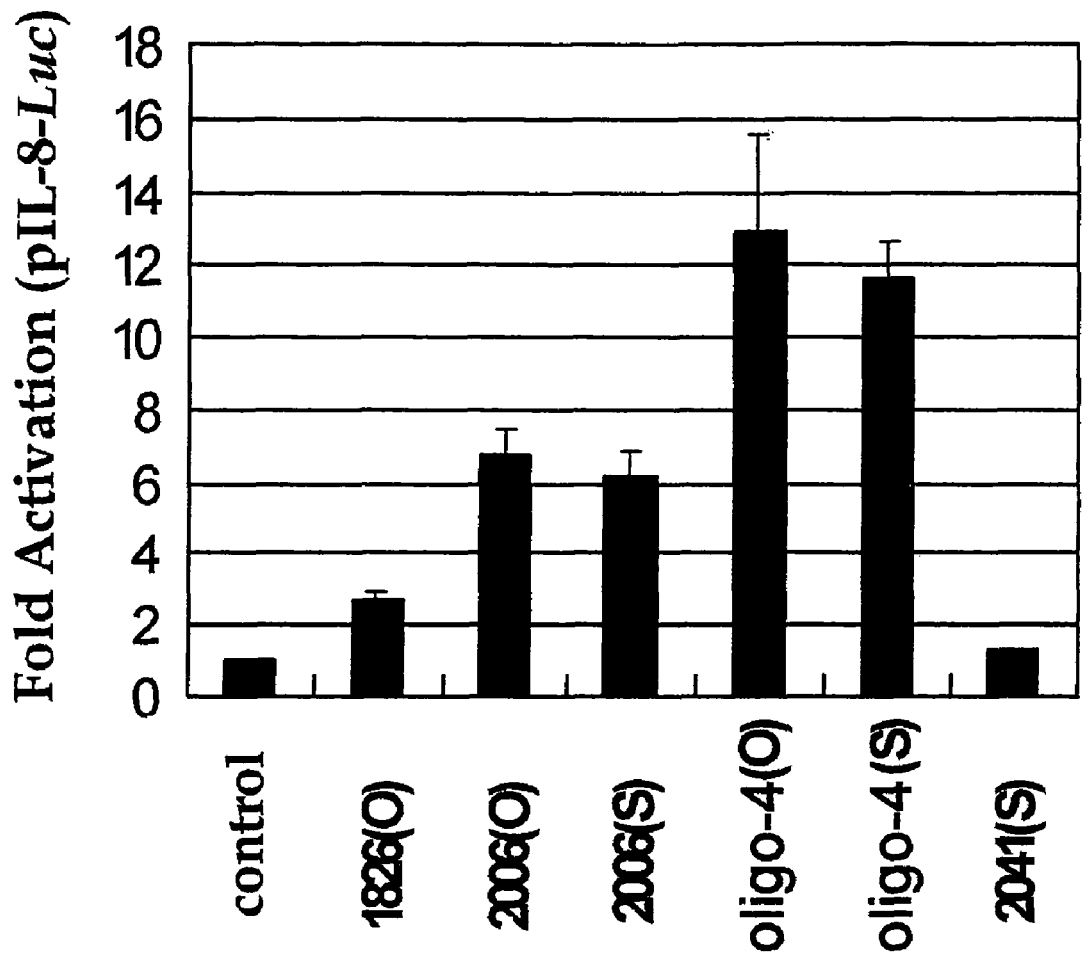
FIG. 2 shows the effect of the backbone modification in the oligo-4 CpG ODN of the present invention upon the activation of IL-8 promoter, as compared to CpG ODNs (1826 and 2006) according to the prior art and non-CpG ODN (2041).

As a result of the experiment, as shown in FIG. 2, activation patterns of the IL-8 promoter were different depending on the nucleotide sequence of CpG ODN. The oligo-4 CpG ODN of the present invention showed the highest activity regardless of its backbone structure (O-type as well as S-type).

<2-2> Comparative Assay for Cytokine Production

Leucocytes were collected from the human peripheral blood, and were applied to each well at a concentration of $1.0 \times 10^6$ cells/well. Next, each well was treated with the O-type or S-type oligo-4 CpG ODN (0 or 10 µg/ml), followed by culture for 24 hours. As a control, the same control as described in the above Example <2-1> was used. After the completion of the culture, the cell culture solution was separated. Then, in order to determine cytokine level in the cell culture solution, sandwich ELISA assay was performed by using commercially available human IL-12 p40 reagent (R&D systems, Minneapolis, USA) and human IFN-γ Quantikine M reagent (R&D systems, Minneapolis, USA), respectively.

An antibody to each cytokine (IL-12 p40 and IFN-γ) was diluted with carbonate buffer (SIGMA, C-3041), and the resultant dilution was coated on the surface of a 96-well plate (NUNC. 442404). The surface was blocked with 3% BSA (SIGMA, A-2154). The cell culture solution was diluted in an adequate ratio and applied to each well, followed by culture for 2 hours. A biotinylated secondary antibody was added thereto and allowed to react at 37° C. for 1 hour. Then, SaV-HRP (Pharmingen, 13047E) was added thereto and allowed to react for additional 30 minutes, and then the reaction mixture was washed for color development. Absorbance was calculated at 490 nm. The cytokine level was recorded as the average of two experimental measurements.

As a result of the assay, as shown in FIG. 3, the oligo-4 CpG ODN of the present invention, regardless of its backbone structure, increased the production of IL-12 p40 in the leucocytes to the highest level. Additionally, O-type oligo-4 CpG ODN increased the production of IFN-γ to the highest level. Also, S-type oligo-4 CpG ODN increased the production of IFN-γ in the leucocytes to a higher level compared to other control ODNs.

<2-3> Effect of O-Type Oligo-4 CpG ODN Upon Expression of. Inflammation-Related Cytokines RAW 264.7 cell lines were treated with O-type oligo-4 CpG ODN (10 µl/ml) for 0.5, 1, 2, 3, 8 and 12 hours. For control, the cells were treated with O-type 1826 and 2006 ODNs under the same concentration. Total RNA was extracted from the cells by using the MicroRNA isolation kit (Stratagene, La Jolla, Calif.). From the total RNA (5 µg), cDNA was synthesized using 50U StrataScript reverse transcriptase and oligo(dT) primer (Stratagene, La Jolla, Calif.). Then, PCR was performed using the cDNA amplified from the total RNA as a template and primers specific to each cytokine (TNF-γ, MIP-2, IL-1, IL-5, IL-10, GM-CSF and IL-12) described in the following Table 2. In Table 2, "F" represents a forward primer and "R" represents a reverse primer.

TABLE 2

Primer Sequences for Amplifying Inflammation-Related Cytokines

| Cytokine | nucleotide sequence (5'→3') | SEQ ID No. |
| --- | --- | --- |
| TNF-α | F: TCTCATCAGTTCTATGGCCC | 21 |
|  | R: GGGAGTAGAGAAGGTACAAC | 22 |
| MIP-2 | F: TGGGTGGGATGTAGCTAGTTCC | 23 |
|  | R: AGTTTGCCTTGACCCTGAAGCC | 24 |
| IL-1 | F: TTGACGGACCCCAAAAGATG | 25 |
|  | R: AGAAGGTGCTCATGTCCTCA | 26 |
| IL-6 | F: GTTCTCTGGGAAATCGTGGA | 27 |
|  | R: TGTACTCCAGGTAGCTATGG | 28 |
| IL-10 | F: ATGCAGGACTTTAAGGGTTA | 29 |
|  | R: ATTTCGGAGAGAGGTAGAAACGACCTTT | 30 |
| GM-CSF | F: ATGTGGCTGCAGAATTTACTTTTCCT | 31 |
|  | R: TGGGCTTCCTCATTTTTGGCCTGGT | 32 |
| IL-12 | F: CTGGTGCAAAGAAACATGG | 33 |
|  | R: TGGTTTGATGATGTCCCTGA | 34 |

PCR amplification was repeated thirty times, wherein one cycle of PCR consisted of DNA denaturation at 94° C. for 30 seconds, primer annealing at 57° C. for 40 seconds, and DNA elongation at 72° C. for 1 minute. As an internal control, expression of GAPDH was also examined.

As a result of the experiment, as shown in FIG. 4, treatment with the O-type oligo-4 CpG ODN of the present invention induced the expression of TNF-γ, MIP-2, IL-1 and IL-12. Particularly, IL-12, which is a typical cytokine inducing a Th1 immune response in the Th1/Th2 immune response balance, was induced only by the oligo-4 CpG ODN of the present invention. This indicates that the CpG ODN of the present invention can induce a Th1 immune response.

As can be seen from the above results, the CpG ODN of the present invention shows high immunoactivity regardless of its backbone structure, contrary to conventional CpG ODNs.

Example 3

In Vitro Assay for Immune Responses Related with Atopic Dermatitis

<3-1> Assay for Activation of Dendritic Cells

The CpG ODN of the present invention was examined to determine whether it activates the dendritic cells isolated from an atopic dermatitis model animal.

a) Isolation of Dendritic Cells and CpG ODN Treatment

Progenitor cells were isolated from the bone marrow of the femoral region of the NC/Nga mouse (SLC, Hamatsu, Japan), which is an atopic dermatitis model animal. To the isolated progenitor cells, RBC lysis buffer (150 mM $NH_4Cl$, 10 mM potassium carbonate, 0.1 mM EDTA pH 7.4) was added, and the reaction mixture was allowed to react at room temperature for 5 minutes. Next, the cells were collected by centrifugation, and were washed with serum-free RPMI medium three times. The cells were stained with trypan blue and the number of the cells was counted with a hematocytometer. The cells were applied to a 6-well plate (Nunc) at a concentration of $2\times10^6$ cells/well. To differentiate the progenitor cells of the bone marrow into dendritic cells, 10% FBS-containing RPMI medium, to which IL-4 and GM-CSF (biosource) were added at a concentration of 10 ng/ml, was added to each well (Ghosh, M., J. Immunol. 170: 5625-5629, 2003). The cells were cultured in an incubator at 37° C. under 5% $CO_2$. The cells were cultured for 6 days, while the medium was changed every other day. Then, the cells were treated with the O-type CpG ODN of the present invention with variable concentrations (4 μg/ml). As the CpG ODN, O-type oligo-4 CpG ODN (SEQ ID NO. 2) and O-type oligo-4-11 ODN (SEQ ID NO. 8), which undergoes modification to the highest degree in the nucleotide sequence of the oligo-4 CpG ODN, were used. Negative control was not subjected to any treatment. Positive control was treated with LPS (100 ng/ml).

b) FACS Assay

The dendritic cells treated with the CpG ODNs (O-type backbone) or with LPS in the above part a) were collected from the cell culture solution and then washed. Next, each antibody (Pharmingen) to MHC class H, CD80 and CD86, which are surface molecules of the dendritic cells was added to the cell suspension, and the reaction mixture was allowed to react at 4° C. for 30 minutes. The supernatant was removed by centrifugation and the remaining cells were washed with PBS once. Further, secondary antibodies to MHC class 11, CD80 and CD86, i.e. anti-hamster IgG2 (secondary antibody to CD80, BD pharmingen; and anti-rat IgG2a (secondary antibody to CD86 and MHC class II, BD pharmingen) were added thereto, and the resultant mixture was allowed to react at 4° C. for 30 minutes. The cells were obtained by centrifugation and then washed. Then, the cells were stained by the PI staining method and were examined for activation degrees of the surface molecules by way of FACS assay.

As a result of the assay, as shown in FIG. 5, all of the surface molecules of dendritic cells were activated in the groups treated with the O-type CpG ODNs (oligo-4 and oligo-4-11), in the same manner as the group treated with LPS. Also, it can be seen that the CpG ODNs according to the present invention can activate the surface molecules of dendritic cells in a concentration-dependent manner (see FIG. 6). It can be seen from the above results that the CpG ODN of the present invention induces the dendritic cells that can activate in vivo immunity.

<3-2> Assay for Expression of Cytokines in Dendritic Cells

RT-PCR was performed in order to examine the expression of IL-12 in the dendritic cells treated with the O-type CpG ODN of the present invention.

First, the dendritic cells isolated from the NC/Nga mouse, which is an atopic dermatitis model animal, in the above example <3-1> were treated with the O-type oligo-4 CpG ODN at different times (0, 0.05, 1, 2, 4 and 8 hours). The controls were treated with 1826 CpG ODN and 2041 non-CpG ODN, respectively. It is known that the 1826 CpG ODN induces the expression of 11-12 to a high level when it is modified to have the S-type backbone (Lee, K W. et al., Mol. Immunol. 41:955-964, 2004). Next, total RNA was isolated from the dendritic cells by way of TRIzol (Invitrogen). The total RNA (5 μg) was treated with M-MLV reverse transcriptase (Invitrogen) and allowed to react at 37 t for 1 hour. The reaction mixture was inactivated at 74° C. for 5 minutes to prepare cDNA. PCR was performed by using the cDNA as a template and a set of primers (SEQ ID NOs. 33 and 34) specific to IL-12. PCR amplification was repeated 25 times, wherein one cycle of PCR consisted of DNA denaturation at 95° C. for 30 seconds, primer annealing at 57° C. for 40 seconds and DNA elongation at 72° C. for 1 minute. After the completion of the PCR reaction, the amplified PCR product was determined on a 1% agarose gel. As a result of the experiment, as shown in FIG. 7, IL-12 expression was induced only by the O-type CpG ODN of the present invention. Meanwhile, contrary to the S-type 1826 CpG ODN, which is known to induce expression of IL-12 to a high degree (Lee, K W. et al., Mol. Immunol. 41:955-964, 2004), O-type 1826 CpG ODN could not induce expression of IL-12.

<3-3> Assay for Induction of Proliferation of Immune Cells a) Induction of T lymphocyte Proliferation The following experiment was performed to examine whether the CpG ODN of the present invention induces T lymphocyte proliferation.

Dendritic cells were isolated from the bone marrow of the femoral region of the NC/Nga mouse (SLC, Hamatsu, Japan), which is an atopic dermatitis model animal, and cultured for 6 days. Next, the dendritic cells were treated with the O-type oligo-4 and oligo-4-11 CpG ODNS at a concentration of 16 μg/ml for 48 hours. The control was not treated with CpG ODN. After 48 hours, the dendritic cells were irradiated with γ-rays at a dose of 20 Gray, and the cells were plated at a concentration of $1.0\times10^4$ cells/well in a round-bottom 96-well plate. Next, to the dendritic cells plated in each well of the plate, T lymphocytes (isolated from the spleen of the NC/Nga mouse) were added as responders in a ratio of 0:1 or 1:10 to a concentration of $1.0\times10^5$ cells/well, followed by culture in an incubator (37° C., 5% $CO_2$) for 96 hours. Then, [$^3$H]thymidine (1 μCi; Amersham, USA) was added to each well, and then allowed to react for 16 hours. The cells were collected from each well on filter paper by using a cell harvester, followed by drying at room temperature. Next, an aqueous scintillation counter (Amersham, USA) was applied to a vial in an amount of 2 ml per vial, and the above filter paper was introduced into the vial so as to be dissolved therein. The cpm (counter per minute) value was measured by using a 13-counter. Each value was obtained by repeating the measurement three times.

As a result of the experiment, as shown in FIG. 8, the O-type CpG ODN of the present invention induced the proliferation of T lymphocytes from dendritic cells. This indicates that the CpG ODNs (oligo-4 and oligo-4-11) can enhance immunity through the proliferation of T lymphocytes, when they are administered to a patient suffering from atopic dermatitis.

b) Induction of Proliferation of Peripheral Blood Mononuclear Cells (PBMCs)

It was reported that AMLR (autologous mixed lymphocyte reaction) is decreased in the peripheral blood collected from a patient suffering from atopic dermatitis (Leung D Y M., J. Clin., Invest., 72:1482-1486, 1983). Hence, the present inventors examined whether the CpG ODN of the present invention induces the proliferation of PBMCs isolated from a patient suffering from atopic dermatitis.

PBMCs were isolated from the blood of a patient suffering from atopic dermatitis by using Histopaque-1077 (Sigma, Poole, UK). The isolated PMBCs were added to a 96 well round-bottom plate at a concentration of $3 \times 10^5$ cells/well. The O-type CpG ODNs (oligo-4 and oligo-4-11) according to the present invention were added to each well, respectively, and allowed to react in an incubator (37° C. 5% $CO_2$) for 72 hours. Then, [$^3$H]thymidine (1 μCi; Amersham, USA) was added to each well, and then the resultant mixture was allowed to react for 16 hours. The cells were collected from each well on filter paper by using a cell harvester, followed by drying at room temperature. Next, an aqueous scintillation counter (Amersham, USA) was applied to a vial in an amount of 2 ml per vial, and the above filter paper was introduced into the vial so as to be dissolved therein. The cpm (counter per minute) value was measured by using a β-counter.

As a result of the experiment, as shown in FIG. 9, the CpG ODNs according to the present invention increase the proliferation of PBMCs to a significantly high degree.]

Example 4

Assay for Skin Penetration of CpG ODN of the Present Invention

<4-1> Preparation of Ointment Containing CpG ODN of the Present Invention

The O-type oligo-4 CpG ODN of the present invention was labeled with FITC (fluorescein isothiocyanate) in a conventional manner known to one skilled in the art. Next, 10 mg of the O-type oligo-4 CpG ODN labeled with FITC was mixed with 5 g of petrolatum (Sam-A Pharmaceutical Ind. Co., Ltd., Korea) to prepare an ointment.

<4-2> Assay for Skin Penetration

An atopic dermatitis animal model, i.e., an NC/Nga mouse (SLC, Hamatsu, Japan) was unhaired on its back. Next, the ointment containing 0.5 mg of CpG-ODN, prepared as described in the above Example <4-1>, was applied on the back. Then, on the 1st and 5th day after the application of the ointment, the back skin with a surface area of $1.5 \times 1.5 \, cm^2$ was removed from the mouse and frozen with liquid nitrogen. Next, the frozen product was embedded into the Tissue-Tek OCT compound (Sakura Finetek USA, INC.), and cut into a thickness of 5 μm by using a cryostat. The tissue section was observed under a fluorescence microscope.

As a result of the observation, as shown in FIG. 10A, the O-type CpG ODN of the present invention penetrated into the mouse skin and remained therein even after a lapse of 5 days starting from the point of application. Additionally, 24 hours after the application, the CpG ODN penetrates into lymph nodes (see FIG. 10B).

Example 5

In Vivo Assay for Determining Effect of Treating Atopic Dermatitis

<5-1> Application of Ointment Containing CpG ODN of the Present Invention

Six NC/Nga mice were divided into two groups: CpG ODN-treated group and non-treated group. To the mice in the treated group, the ointment containing the O-type oligo-4 CpG ODN, prepared as described in the above Example <4-1> (0.2 mg CpG-ODN per mouse), was applied onto the atopic dermatitis lesion present in the back of the mice. To the mice in the non-treated group, petrolatum containing no CpG ODN of the present invention was applied under the same condition.

<5-2> Observation of Lesions

On the $5^{th}$ and $7^{th}$ day after the application of the CpG ODN-containing ointment, the atopic dermatitis lesions were observed with the naked eyes. As a result of the observation, as shown in FIG. 11A, the mice treated with the O-type CpG ODN of the present invention showed a disappearance of atopic dermatitis lesions on their backs, compared with the mice in the non-treated group. Additionally, the back skin was removed and stained by using the H&E staining method to examine the effect of treating atopic dermatitis. As a result of the examination, as shown in FIG. 11B, the lesions of the mice treated with the O-type CpG ODN of the present invention showed a significant decrease in hyperkeratosis and acanthosis, as well as in infiltration of lymphocytes in the dermis (magnification ×200). Therefore, it can be seen that atopic dermatitis can be treated effectively by using the CpG ODN of the present invention.

<5-3> Histochemical Assay a) Assay for Expression of Cytokines

On the $5^{th}$ day after the application of the ointment containing the O-type CpG ODN of the present invention, the mouse skin with a surface area of $1.5 \times 1.5 \, cm^2$ was removed. Next, the skin was fixed in 4% formalin solution for at least 1 day. The fixed skin tissue was treated with paraffin and cut into a thickness of 5 μm. After removing the paraffin, the following experiment was performed with the skin sample according to the manual provided by the LSAB+ kit (DAKO, Denmark). The sample was treated with 3% $H_2O_2$ for 10 minutes. Next, 10% normal goat sera diluted with TBS (Tris-buffered saline, pH 7.4) containing 0.1% BSA was added thereto to block the sample at room temperature for 1 hour. After washing with PBS (pH 7.4), the sample was treated with the primary antibodies, i.e. goat anti-mouse IL-10, goat anti-mouse IL-4 (Santa Cruz, USA), and rat anti-mouse IFN-γ (Pierce, USA), and allowed to react at 4° C. for at least 12 hours. Then, biotin-labeled secondary antibodies were added thereto and allowed to react at room temperature for 30 minutes. Next, peroxidase-labeled streptavidin was added thereto, and allowed to react at room temperature for about 30 minutes. After carrying out staining with DAB substrate chromogen system (DAKO, Denmark), the sample was observed with a microscope (magnification ×200).

According to the observation, as shown in FIG. 12, the epidermis of the mouse, after 5 days of treatment with the inventive O-type CpG ODN, showed a decrease in the expression of IL-4 and IL-10. On the contrary, there was an increase in the expression of IFN-γ. This indicates that the O-type CpG ODN of the present invention decreases the production of cytokine mediated by Th2 phenotype T lymphocytes which are specifically high in atopic dermatitis, IL-4 and IL-10. On the other hand, the inventive CpG ODN increases the production of cytokine mediated by Th1 phenotype T lymphocytes, IFN-γ. By doing so, the inventive CpG ODN improves the condition of atopic dermatitis and treats atopic dermatitis.

b) Staining of $CD4^+$ and $CD8^+$ Lymphocytes in Tissue

On $5^{th}$ day after the application of the ointment containing the O-type CpG ODN of the present invention, the mouse skin with a surface area of $1.5 \times 1.5 \, cm^2$ was removed. The skin tissue was frozen with liquid nitrogen. Next, the frozen tissue was embedded in the Tissue-Tek OCT compound (Sakura Finetek USA, INC.), and was cut into a thickness of 5 μm by using a cryostat. The tissue was allowed to react with the primary antibodies, i.e. rat anti-mouse CD4 mAb (BD phamingen, USA) or rat anti-CD8 mAb (serotec, UK) at 4° C. for 12 hours. Then, biotin-labeled secondary antibodies were added thereto and allowed to react at room temperature for 30 minutes. Next, peroxidase-labeled streptavidin was added thereto, and the reaction mixture was allowed to react at room temperature for about 30 minutes. After carrying out staining with DAB substrate chromogen system (DAKO, Denmark), the sample was observed under a microscope (magnification × 200).

As a result of the observation, as shown in FIG. 13, the mouse skin treated with the O-type CpG ODN of the present invention showed a decrease in the number of $CD4^+$ and $CD8^+$ Lymphocyte cells. The decrease in the number of $CD4^+$ and $CD8^+$ Lymphocytes in a lesion of atopic dermatitis is a therapeutically favorable phenomenon (Christian V., et al. *J Clin Invest* 104:1907-1105, 1999).

<5-4> Assay for IgE Level in Blood Sera

After the mice in each group were anesthetized with ether, blood was collected from the vena cava of the mice and introduced into a heparinized tube. Next, centrifugation was performed at 1000 g for 10 minutes to obtain blood plasma, and the blood plasma was stored at −20° C. until it is used. The total IgE level was measured by using the Mouse IgE BD OptEIA Kit (BD phamingen, USA). The measurement was performed according to the manufacturer's protocol provided by the BD OptEIA Kit. First, 100 μl of the IgE capture antibody (capture Ab) were added to each well of a 96-well plate and allowed to react at 4° C. for at least 12 hours. The solution present in each well was removed and the well was washed with washing buffer (PBS with 0.05% Tween-20) three times. Then, 200 μl of blocking buffer (PBS with 10% FBS) was added to each well and was allowed to react at room temperature for 1 hour. The blocking buffer was removed, followed by washing the well with the above washing buffer three times. The plasma sample obtained from each mouse was added to each well in an amount of 100 μl, and then allowed to react at room temperature for 2 hours. Next, the solution present in each well was removed and the well was washed with the above washing buffer five times. Then, 100 μl of the biotinylated mouse IgE antibody (BD Pharmingen, USA) conjugated with avidin-horseradish peroxidase (avidin-HRP), was added to each well, and allowed to react at room temperature for 1 hour. After the completion of the reaction, the well was washed seven times. Then, 100 μl of the TMB substrate solution (BD pharmingen, USA) were added to each well, and was allowed to react in the dark at room temperature for 30 minutes. Next, 50 μl of 1M phosphoric acid (BD pharmingen, USA) were added to each well as a stop solution. The solution in each well was measured for the absorbance at 450 nm by using an ELISA reader, within 30 minutes of stopping reaction.

As a result of the measurement, as shown in FIG. 14, the mice treated with the ointment containing the O-type CpG ODN of the present invention showed a significant decrease in the serum IgE level.

As can be seen from the above results, the O-type CpG ODN of the present invention decreases the expression of cytokines mediated by Th2-lymphocytes, while it increases the expression of cytokines mediated by Th1-lymphocytes. Hence, the inventive CpG ODN decreases the serum IgE level, so that it is highly effective for the treatment of atopic dermatitis.

Example 6

Recovery Effect of CpG-ODN Upon Ultraviolet Radiation-Induced Immunosuppression of Delayed-Type Hypersensitivity in Mice 8-weeks old female Balb/c mice (body weight of about 20 g, Korea SLC, KR) were divided into the following five groups, each group including five mice.

(1) Negative Control: neither UV irradiation nor sensitization was treated.

(2) Positive Control: UV irradiation was not used, but sensitization was treated.

(3) UV Treatment Group: mice were irradiated with UV rays, and then sensitized after 3 days of UV irradiation.

(4) Oligo-4 Treatment Group: the O-type oilgo-4 according to the present invention was injected to mice via an intraperitoneal route, after 24 hours of UV irradiation, and then the mice were sensitized after 3 days of UV irradiation.

(5) Oligo-11 Treatment Group: the O-type oilgo-11 according to the present invention was injected to mice via an intraperitoneal route, after 24 hours of UV irradiation, and then the mice were sensitized after 3 days of UV irradiation.

Mice were shaved on their backs to perform UV irradiation, as well as on their bellies to induce sensitization. The procedures for carrying out the experiment are shown in FIG. 15.

Mice in each group were put into a UV box equipped with a UV B lamp (4FSX24T12/UVB-HO, UBL, USA), and irradiated with UV rays at a dose of 0.6 mW/cm² for 28 minutes. The total energy of the UVB rays irradiated to the mice was 10 KJ/m². By doing so, the immunosuppression of delayed-type hypersensitivity was induced by UV irradiation. Then, after 24 hours of UV irradiation, the CpG ODNs according to the present invention, dissolved in PBS at a concentration of 1 mg/ml was injected intraperitoneally to the mice at a dose of 20 μg. To the control, the same amount of PBS solution was injected.

After two days of the injection, 100 μl of 3% TNCB solution (Trinitrochlorobenzene; Tokyo Kasei Co., Tokyo, Japan) was applied to the abdomen of each female hair-shaved Balb/c mouse, so as to induce a sensitization. After five days of the sensitization, each mouse was measured for its ear thickness. 1% TNCB solution was further applied to both ears of each mouse in order to induce ear swelling again. After 24 hours, edema of mouse ears was then measure using a micrometer (Mitutyo, Tokyo, Japan).

As a result of the measurement, as shown in FIG. 16, application of 100 a of 3% TNCB onto the belly of the unhaired mouse induced contact hypersensitivity in the mice (positive control: $18.5 \pm 3.73 \times 10^{-2}$ mm). In the mice irradiated with UV rays, the degree of edema in mouse ear decreased ($8.3 \pm 1.66 \times 10^{-2}$ mm). Meanwhile, intraperitoneal injection of the inventive CpG ODN resulted in significant recovery of the contact hypersensitivity suppressed by UV rays. This indicates that the CpG ODN of the present invention can recover immune responses suppressed by UV rays.

Example 7

Effect of CpG ODN of the Present Invention Upon Induction of Proliferation Responses of TNP-Specific Antigen T Cells Isolated from Spleen of Mice in which Contact Hypersensitivity is Suppressed by UV Irradiation 8-weeks old female Balb/c mice (body weight of about 20 g) were divided into five groups (negative control, positive control, UV treatment group, oligo-4 treatment group and oligo-11 treatment group), each group including five mice. UV irradiation, treatment with the inventive CpG ODN and sensitization were carried out in the same manner as described in Example 6. To induce an antigen-specific response, spleen cells isolated from the mice of the negative control, in which neither UV irradiation nor sensitization was treated, were allowed to conjugate with 10 mM $TNBSO_3$ (trinitrochlorobenzensulfonic acid; Tokyo Kasei Co., Tokyo; Japan). The conjugated cells were used as stimulator cells. Meanwhile, spleen cells isolated from the mice in the positive control, UV treatment group, UV irradiation/oligo-4 treatment group and UV irradiation/oligo-11 treatment group were used as responder cells. The responder cells were plated in each well of a round-bottom 96-well plate at a concentration of 1×10⁵ cells/well. Then, the stimulator cells were added to each well, followed by culture for 5 days. The stimulator cells and the responder cells were mixed in a ratio of 1:1. Then, before 18 hours of cell harvest, 0.5 μCi of [$^3$H]thymidine was added to each well, and allowed to react for 18 hours. The cells were harvested by using a cell harvester and collected on filter paper, followed by drying at room temperature. Next, an aqueous scintillation counter (Amersham Biosciences, USA) was applied to a vial in an amount of 2 ml, so that the filter paper was dissolved therein. Then, a cpm (counter per minute) value was measured by using a β-scintillation counter (Amersham Biosciences, USA), so as to examine the proliferation degree of the immune cells (T cells) isolated from the mouse spleen.

As a result of the examination, as shown in FIG. 17, the TNP (trinitrophenyl)-specific antigen T cell proliferation responses in the T cells isolated from the mouse, in which contact hypersensitivity to the specific antigen (TNCB) is suppressed by UV irradiation, is increased significantly by the treatment with the CpG ODN of the present invention. This indicates that the immunosuppression effect caused by UV rays in a contact dermatitis model can be recovered significantly by the CpG ODN of the present invention.

<Application 1>

Skin Disease Caused by Virus

Viral skin disease occurs frequently in humans with low immunity or patients suffering from chronic diseases. In such humans or patients, type 1 T cell immune responses decrease, while type 2 T cell immune responses increase (Hengge U. R., et al., *Br J Dermatol.,* 149: 15-19, 2003; Katakura T., et al., *Clinical Immunol,* 105: 363-370, 2002). Such viral diseases include molluscum contagiosum, Verruca/condyloma, herpes virus infection, or the like, and can be treated effectively by way of direct injection of IL-12 or by way of the treatment for increasing IL-12 level (Arany I., et al., *Antiviral Res.,* 43: 55-63, 1999; Matsuo, R., et al., 59:623-630, 1996; and Katakura, T., et al., *Clin. Immunol.* 105:363-370, 2002). Therefore, the CpG ODN of the present invention, which has an effect of increasing IL-12 level, is very effective for the treatment of viral skin diseases.

<Application 2>

Skin Cancer

Skin cancer occurs frequently in humans with low immunity or immunosuppression. It is reported that, in such humans, especially, a Th1 immune response participating in cell-mediated immunity decreases, while a Th2 immune response increases (Rook A H., et al., *Ann N Y Acad. Sci.,* 795: 310-318, 1996). IL-12 is known as a cytokine that causes immune responses to infection and cancer, and thus treats them(?). Such effect is provided by the in vivo production of IFN-γ (Trinchieri G., et al., *Annu Rev Immunol,* 13: 251-276, 1995). It is also reported that IL-12 can be used for the treatment of skin cancers and CpG-ODN is effective for the treatment of malignant melanoma (Gollob J A., et al., *J Clin Oncology.,* 21: 2564-2573, 2003; Krepler C., et al., *J invest Dermatol.,* 122: 387-391, 2004). Therefore, the CpG ODN of the present invention, which has an effect of increasing IL-12 level, is very effective for the treatment of skin cancer.

<Application 3>

Atopic Dermatitis and Allergic Skin Disease

Although the etiology of atopic dermatitis is not defined up to date, it is thought that allergen-specific T cells that produce Th2 cytokines including IL-4 and IL-5 cause atopic dermatitis. Moreover, it is demonstrated that such cells infiltrate into the lesions in patients suffering from atopic dermatitis (Neumann C., et al., *J Mol Med.,* 74: 401-406, 1996). It is also reported that when the monocytes of patients suffering from atopic dermatitis or dendritic cells derived from the monocytes are stimulated with LPS (lipopolysaccharide), IL-12p40 production is significantly decreased compared to normal persons (Aiba S., et al., *Exp Dermatol.,* 12: 86-95, 2003). Further, it is reported that a decreased number of monocytes producing IL-12 from the umbilical cord blood of infants is related with IgE production, and atopic dermatitis occurs frequently under the same conditions (Nilsson C., et al., *Clin Exp Allergy.,* 34: 373-380, 2004). Therefore, the CpG-ODN based on the present invention, which increases IL-12 production in dendritic cells, is expected to be effective for the treatment of atopic dermatitis and IgE-increasing allergic skin diseases, especially considering that one of the important factors determining Th1/Th2 immune responses is IL-12.

INDUSTRIAL APPLICABILITY

As can be seen from the foregoing, the CpG ODNs according to the present invention induce an effective immune response for the treatment or prevention of skin diseases, regardless of their backbone structures. Therefore, the CpG ODNs, particularly O-type CpG ODNs according to the present invention can be used as a therapeutic agent for treating or preventing a skin disease.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

What is claimed is:

1. A method of inhibiting a Th2 cytokine and inducing a Th1 cytokine comprising administering to a subject an effective amount of an isolated CpG oligonucleotide, wherein said oligonucleotide consists of a sequence selected from the group consisting of sequences set forth in SEQ ID NOS:2-8, wherein the CpG oligonucleotide comprises at least two unmethylated CpG motifs, and wherein said administering results in inhibition of a Th2 cytokine and induction of a Th1 cytokine in said subject.

2. The method according to claim 1, wherein the Th2 cytokine is IL-4 or IL-10.

3. The method according to claim 1, wherein the Th1 cytokine is IL-12 or IFN-γ.

4. The method according to claim 1, wherein the CpG oligodeoxynucleotide has a phosphodiester or phosphorothioate backbone.

5. A method for stimulating an immune response comprising administering to a subject an effective amount of an isolated CpG oligonucleotide, wherein said oligonucleotide consists of a sequence selected from the group consisting of sequences set forth in SEQ ID NOS:2-8, wherein the CpG oligonucleotide comprises at least two unmethylated CpG motifs, wherein said administering result in stimulation of an immune response in said subject, and wherein said immune response is mediated by inhibiting a Th2 cytokine and inducing a Th1 cytokine.

6. The method according to claim 5, wherein the CpG oligodeoxynucleotide has a phosphodiester or phosphorothioate backbone.

7. A method for treating atopic dermatitis associated with an increase in Th2 cytokines and a decrease in Th1 cytokines in a subject comprising administering to a subject with said atopic dermatitis an effective amount of an isolated CpG oligodeoxynucleotide consisting of a sequence selected from the group consisting of sequences set forth in SEQ ID NO:2-8, wherein the CpG oligonucleotide comprises at least two unmethylated CpG motifs, and wherein said administering is correlated with an improvement of symptoms of said atopic dermatitis in said subject.

8. The method according to claim 7, wherein the CpG oligodeoxynucleotide has a phosphodiester or phosphorothioate backbone.

9. A composition for treating atopic dermatitis associated with an increase in Th2 cytokines and a decrease in Th1 cytokines comprising an isolated CpG oligonucleotide consisting of a sequence selected from the group consisting of sequences set forth in SEQ ID NO:2-8, wherein said oligonucleotide comprises at least two unmethylated CpG motifs.

* * * * *

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial sequence
<220> FEATURE:
<223> OTHER INFORMATION: CpG ODN
<220> FEATURE:
<221> NAME/KEY: misc_feature
<222> LOCATION: (1)..(1)
<223> OTHER INFORMATION: s is g or c
```

```
<220> FEATURE:
<221> NAME/KEY: misc_feature
<222> LOCATION: (2)..(3)
<223> OTHER INFORMATION: y is c or t
<220> FEATURE:
<221> NAME/KEY: misc_feature
<222> LOCATION: (4)..(5)
<223> OTHER INFORMATION: s is g or c
<220> FEATURE:
<221> NAME/KEY: misc_feature
<222> LOCATION: (11)..(11)
<223> OTHER INFORMATION: s is g or c
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: y is c or t
<220> FEATURE:
<221> NAME/KEY: misc_feature
<222> LOCATION: (14)..(14)
<223> OTHER INFORMATION: r is g or a
<220> FEATURE:
<221> NAME/KEY: misc_feature
<222> LOCATION: (16)..(16)
<223> OTHER INFORMATION: w is a or t
<220> FEATURE:
<221> NAME/KEY: misc_feature
<222> LOCATION: (17)..(17)
<223> OTHER INFORMATION: m is a or c
<220> FEATURE:
<221> NAME/KEY: misc_feature
<222> LOCATION: (18)..(18)
<223> OTHER INFORMATION: y is c or t

<400> SEQUENCE: 1
syyssacgtt snyrawmytc                                               20

<210> SEQ ID NO 2
<211> LENGTH: 20
<212> TYPE: DNA
<213> ORGANISM: Artificial sequence
<220> FEATURE:
<223> OTHER INFORMATION: oligo-4 CpG ODN

<400> SEQUENCE: 2
ctcgcacgtt gccgaacttc                                               20

<210> SEQ ID NO 3
<211> LENGTH: 20
<212> TYPE: DNA
<213> ORGANISM: Artificial sequence
<220> FEATURE:
<223> OTHER INFORMATION: oligo 4-3 CpG ODN

<400> SEQUENCE: 3
ctcgcacgtt gctgaacttc                                               20

<210> SEQ ID NO 4
<211> LENGTH: 20
<212> TYPE: DNA
<213> ORGANISM: Artificial sequence
<220> FEATURE:
<223> OTHER INFORMATION: oligo 4-4 CpG ODN

<400> SEQUENCE: 4
ctcgcacgtt gccaaacttc                                               20

<210> SEQ ID NO 5
<211> LENGTH: 20
```

```
<212> TYPE: DNA
<213> ORGANISM: Artificial sequence
<220> FEATURE:
<223> OTHER INFORMATION: oligo 4-8 CpG ODN

<400> SEQUENCE: 5
ctcgcacgtt gacgaacttc                                              20

<210> SEQ ID NO 6
<211> LENGTH: 20
<212> TYPE: DNA
<213> ORGANISM: Artificial sequence
<220> FEATURE:
<223> OTHER INFORMATION: oligo 4-9 CpG ODN

<400> SEQUENCE: 6
ctcgcacgtt gtcgaacttc                                              20

<210> SEQ ID NO 7
<211> LENGTH: 20
<212> TYPE: DNA
<213> ORGANISM: Artificial sequence
<220> FEATURE:
<223> OTHER INFORMATION: oligo 4-10 CpG ODN

<400> SEQUENCE: 7
ctcgcacgtt cgcgaacttc                                              20

<210> SEQ ID NO 8
<211> LENGTH: 20
<212> TYPE: DNA
<213> ORGANISM: Artificial sequence
<220> FEATURE:
<223> OTHER INFORMATION: oligo 4-11 CpG ODN

<400> SEQUENCE: 8
gctcgacgtt ggcgatactc                                              20

<210> SEQ ID NO 9
<211> LENGTH: 20
<212> TYPE: DNA
<213> ORGANISM: Artificial sequence
<220> FEATURE:
<223> OTHER INFORMATION: oligo 4-1 CpG ODN

<400> SEQUENCE: 9
ctcgcacatt gccgaacttc                                              20

<210> SEQ ID NO 10
<211> LENGTH: 20
<212> TYPE: DNA
<213> ORGANISM: Artificial sequence
<220> FEATURE:
<223> OTHER INFORMATION: oligo 4-2 CpG ODN

<400> SEQUENCE: 10 ctcgcactt gccgaacttc                                               20

<210> SEQ ID NO 11
<211> LENGTH: 20
<212> TYPE: DNA
<213> ORGANISM: Artificial sequence
<220> FEATURE:
<223> OTHER INFORMATION: oligo 4-5 CpG ODN

<400> SEQUENCE: 11
ctcgcacgaa gccgaacttc                                              20
```

```
<210> SEQ ID NO 12
<211> LENGTH: 20
<212> TYPE: DNA
<213> ORGANISM: Artificial sequence
<220> FEATURE:
<223> OTHER INFORMATION: oligo 4-6 CpG ODN

<400> SEQUENCE: 12
ctcgcacgcc gccgaacttc                                         20

<210> SEQ ID NO 13
<211> LENGTH: 20
<212> TYPE: DNA
<213> ORGANISM: Artificial sequence
<220> FEATURE:
<223> OTHER INFORMATION: oligo 4-7 CpG ODN

<400> SEQUENCE: 13
ctcgcacggg gccgaacttc                                         20

<210> SEQ ID NO 14
<211> LENGTH: 27
<212> TYPE: DNA
<213> ORGANISM: Artificial sequence
<220> FEATURE:
<223> OTHER INFORMATION: forward primer for IL-8 promoter

<400> SEQUENCE: 14
gtgagatctg aagtgtgatg actcagg                                 27

<210> SEQ ID NO 15
<211> LENGTH: 27
<212> TYPE: DNA
<213> ORGANISM: Artificial sequence
<220> FEATURE:
<223> OTHER INFORMATION: reverse primer for IL-8 promoter

<400> SEQUENCE: 15
gtgaagcttg aagcttgtgt gctctgc                                 27

<210> SEQ ID NO 16
<211> LENGTH: 25
<212> TYPE: DNA
<213> ORGANISM: Artificial sequence
<220> FEATURE:
<223> OTHER INFORMATION: forward primer for IL-12 promoter

<400> SEQUENCE: 16
catgagctca gcctcccgtc tgacc                                   25

<210> SEQ ID NO 17
<211> LENGTH: 25
<212> TYPE: DNA
<213> ORGANISM: Artificial sequence
<220> FEATURE:
<223> OTHER INFORMATION: reverse primer for IL-12 promoter

<400> SEQUENCE: 17
ctgggctcga gggagagtcc aatgg                                   25

<210> SEQ ID NO 18
<211> LENGTH: 20
<212> TYPE: DNA
<213> ORGANISM: Artificial sequence
<220> FEATURE:
<223> OTHER INFORMATION: O-type 1826 ODN
```

```
<400> SEQUENCE: 18
tccatgacgt tcctgacgtt                                              20

<210> SEQ ID NO 19
<211> LENGTH: 24
<212> TYPE: DNA
<213> ORGANISM: Artificial sequence
<220> FEATURE:
<223> OTHER INFORMATION: O-type 2006 CpG ODN

<400> SEQUENCE: 19
tcgtcgtttt gtcgttttgt cgtt                                         24

<210> SEQ ID NO 20
<211> LENGTH: 24
<212> TYPE: DNA
<213> ORGANISM: Artificial sequence
<220> FEATURE:
<223> OTHER INFORMATION: S-type 2041 non-CpG ODN

<400> SEQUENCE: 20
ctggtctttc tggttttttt ctgg                                         24

<210> SEQ ID NO 21
<211> LENGTH: 20
<212> TYPE: DNA
<213> ORGANISM: Artificial sequence
<220> FEATURE:
<223> OTHER INFORMATION: forward primer for TNF-alpha

<400> SEQUENCE: 21
tctcatcagt tctatggccc                                              20

<210> SEQ ID NO 22
<211> LENGTH: 20
<212> TYPE: DNA
<213> ORGANISM: Artificial sequence
<220> FEATURE:
<223> OTHER INFORMATION: reverse primer for TNF-alpha

<400> SEQUENCE: 22
gggagtagac aaggtacaac                                              20

<210> SEQ ID NO 23
<211> LENGTH: 22
<212> TYPE: DNA
<213> ORGANISM: Artificial sequence
<220> FEATURE:
<223> OTHER INFORMATION: forward primer for MIP-2

<400> SEQUENCE: 23
tgggtgggat gtagctagtt cc                                           22

<210> SEQ ID NO 24
<211> LENGTH: 22
<212> TYPE: DNA
<213> ORGANISM: Artificial sequence
<220> FEATURE:
<223> OTHER INFORMATION: reverse primer for MIP-2

<400> SEQUENCE: 24
agtttgcctt gaccctgaag cc                                           22

<210> SEQ ID NO 25
<211> LENGTH: 20
```

```
<212> TYPE: DNA
<213> ORGANISM: Artificial sequence
<220> FEATURE:
<223> OTHER INFORMATION: forward primer for IL-1

<400> SEQUENCE: 25
ttgacggacc ccaaaagatg                                            20

<210> SEQ ID NO 26
<211> LENGTH: 20
<212> TYPE: DNA
<213> ORGANISM: Artificial sequence
<220> FEATURE:
<223> OTHER INFORMATION: reverse primer for IL-1

<400> SEQUENCE: 26
agaaggtgct catgtcctca                                            20

<210> SEQ ID NO 27
<211> LENGTH: 20
<212> TYPE: DNA
<213> ORGANISM: Artificial sequence
<220> FEATURE:
<223> OTHER INFORMATION: forward primer for IL-6

<400> SEQUENCE: 27
gttctctggg aaatcgtgga                                            20

<210> SEQ ID NO 28
<211> LENGTH: 20
<212> TYPE: DNA
<213> ORGANISM: Artificial sequence
<220> FEATURE:
<223> OTHER INFORMATION: reverse primer for IL-6

<400> SEQUENCE: 28
tgtactccag gtagctatgg                                            20

<210> SEQ ID NO 29
<211> LENGTH: 20
<212> TYPE: DNA
<213> ORGANISM: Artificial sequence
<220> FEATURE:
<223> OTHER INFORMATION: forward primer for IL-10

<400> SEQUENCE: 29
atgcaggact ttaagggtta                                            20

<210> SEQ ID NO 30
<211> LENGTH: 28
<212> TYPE: DNA
<213> ORGANISM: Artificial sequence
<220> FEATURE:
<223> OTHER INFORMATION: reverse primer for IL-10

<400> SEQUENCE: 30
atttcggaga gaggtagaaa cgaccttt                                   28

<210> SEQ ID NO 31
<211> LENGTH: 26
<212> TYPE: DNA
<213> ORGANISM: Artificial sequence
<220> FEATURE:
<223> OTHER INFORMATION: forward primer for GM-CSF

<400> SEQUENCE: 31
atgtggctgc agaatttact tttcct                                     26
```

```
<210> SEQ ID NO 32
<211> LENGTH: 25
<212> TYPE: DNA
<213> ORGANISM: Artificial sequence
<220> FEATURE:
<223> OTHER INFORMATION: reverse primer for GM-CSF

<400> SEQUENCE: 32
tgggcttcct cattttggc ctggt                                             25

<210> SEQ ID NO 33
<211> LENGTH: 19
<212> TYPE: DNA
<213> ORGANISM: Artificial sequence
<220> FEATURE:
<223> OTHER INFORMATION: forward primer for IL-12

<400> SEQUENCE: 33
ctggtgcaaa gaaacatgg                                                   19

<210> SEQ ID NO 34
<211> LENGTH: 20
<212> TYPE: DNA
<213> ORGANISM: Artificial sequence
<220> FEATURE:
<223> OTHER INFORMATION: reverse primer for IL-12

<400> SEQUENCE: 34
tggtttgatg atgtccctga                                                  20
```